(12) United States Patent
Fukumoto et al.

(10) Patent No.: US 10,803,898 B2
(45) Date of Patent: Oct. 13, 2020

(54) FLUORINE-CONTAINING ETHER COMPOUND, LUBRICANT FOR MAGNETIC RECORDING MEDIUM, AND MAGNETIC RECORDING MEDIUM

(71) Applicant: SHOWA DENKO K.K., Tokyo (JP)

(72) Inventors: Naoya Fukumoto, Tokyo (JP); Daisuke Yagyu, Tokyo (JP); Yuta Yamaguchi, Tokyo (JP); Shoko Uetake, Tokyo (JP); Tsuyoshi Kato, Tokyo (JP); Hiroyuki Tomita, Tokyo (JP); Ryuta Miyasaka, Tokyo (JP); Katsumi Murofushi, Tokyo (JP)

(73) Assignee: SHOWA DENKO K.K., Minato-ku, Tokyo (JP)

( * ) Notice: Subject to any disclaimer, the term of this patent is extended or adjusted under 35 U.S.C. 154(b) by 317 days.

(21) Appl. No.: 15/664,013

(22) Filed: Jul. 31, 2017

(65) Prior Publication Data
US 2018/0047419 A1 Feb. 15, 2018

(30) Foreign Application Priority Data
Aug. 10, 2016 (JP) ................. 2016-158134

(51) Int. Cl.
G11B 5/66 (2006.01)
G11B 5/725 (2006.01)
(Continued)

(52) U.S. Cl.
CPC .............. *G11B 5/725* (2013.01); *C07C 43/11* (2013.01); *C07C 43/137* (2013.01);
(Continued)

(58) Field of Classification Search
CPC ............ C10M 107/38; C10M 2213/00; C10M 2213/04; C10M 2213/043; C10M 2213/06;
(Continued)

(56) References Cited

U.S. PATENT DOCUMENTS

2005/0197408 A1\* 9/2005 Shirakawa ........... C08G 65/007
514/723

FOREIGN PATENT DOCUMENTS

CN 1703442 A 11/2005
CN 102356431 A 2/2012
(Continued)

OTHER PUBLICATIONS

First Office Action dated Apr. 16, 2019, from the State Intellectual Property Office of the P.R.C in counterpart application No. 201710665166.9.
(Continued)

*Primary Examiner* — Holly C Rickman
(74) *Attorney, Agent, or Firm* — Sughrue Mion, PLLC

(57) ABSTRACT

A fluorine-containing ether compound of the present invention is represented by Formula (1).

$$R^1-CH_2-R^2-CH_2-R^3 \qquad (1)$$

(In Formula (1), $R^1$ is an organic end group having 3 or more carbon atoms which includes two or more polar groups with each polar group being bonded to different carbon atoms and the carbon atoms to which the polar groups are bonded being bonded to each other via a linking group including the carbon atoms which are not bonded to the polar groups, $R^2$ includes a perfluoropolyether chain represented by Formula (3), and $R^3$ is a hydroxyl group or $R^1$)

$$-(CF_2)_{y-1}-O-((CF_2)_yO)_z-(CF_2)_{y-1}- \qquad (3)$$

(Continued)

(In Formula (3), y represents an integer of 2 to 4, and z represents an integer of 1 to 30).

17 Claims, 1 Drawing Sheet

(51) Int. Cl.
    *C07D 303/28*     (2006.01)
    *C07D 303/18*     (2006.01)
    *C07C 43/11*     (2006.01)
    *C10M 147/04*     (2006.01)
    *C08G 65/00*     (2006.01)
    *C07C 43/13*     (2006.01)
    *C08G 65/26*     (2006.01)
    *C10M 105/54*     (2006.01)
    *C10N 20/04*     (2006.01)
    *C10N 40/18*     (2006.01)
    *C10N 50/00*     (2006.01)

(52) U.S. Cl.
    CPC ......... *C07D 303/18* (2013.01); *C07D 303/28* (2013.01); *C08G 65/007* (2013.01); *C08G 65/2639* (2013.01); *C10M 105/54* (2013.01); *C10M 147/04* (2013.01); *C10M 2211/0425* (2013.01); *C10M 2213/023* (2013.01); *C10N 2020/04* (2013.01); *C10N 2040/18* (2013.01); *C10N 2050/025* (2020.05)

(58) Field of Classification Search
    CPC ........... C10M 2213/0606; G11B 5/725; C10N 2040/18; C10N 2240/204; C08G 65/007; C08G 2650/48; C09D 171/00; C09D 171/02; Y10T 428/1164
    See application file for complete search history.

(56) References Cited

FOREIGN PATENT DOCUMENTS

| | | |
|---|---|---|
| JP | 8-063739 A | 3/1996 |
| JP | 2010-020823 A | 1/2010 |
| JP | 4632144 B2 | 2/2011 |
| JP | 2013-163667 A | 8/2013 |
| JP | 5613916 B2 | 10/2014 |
| JP | 5815896 B1 | 11/2015 |
| WO | 2004/035656 A1 | 4/2004 |
| WO | 2009/035075 A1 | 3/2009 |

OTHER PUBLICATIONS

Chiba et al., "Development of Novel Lubricants for Ultra Low Flying Height", Fujitsu, Jan. 2007, vol. 58.1, pp. 48-52 (total 5 pages).

Notice of Reasons for Rejection dated Mar. 17, 2020 from Japanese Patent Office in JP Application No. 2016-158134.

\* cited by examiner

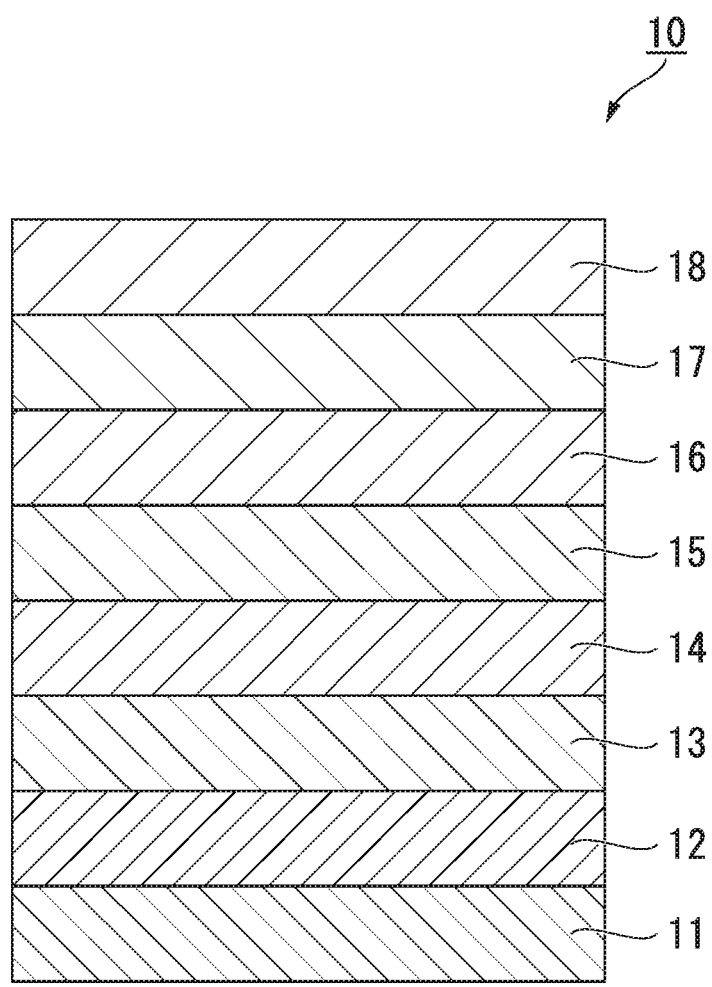

FLUORINE-CONTAINING ETHER COMPOUND, LUBRICANT FOR MAGNETIC RECORDING MEDIUM, AND MAGNETIC RECORDING MEDIUM

BACKGROUND OF THE INVENTION

Field of the Invention

The present invention relates to a fluorine-containing ether compound suitable for application as a lubricant of a magnetic recording medium, a lubricant for a magnetic recording medium including the same, and a magnetic recording medium.

This application claims priority to Japanese Patent Application No. 2016-158134 filed on Aug. 10, 2016, the contents of which are incorporated herein by reference.

Description of Related Art

In order to improve the recording density of magnetic recording/reproducing apparatuses, magnetic recording media suitable for high recording densities are being developed.

In the related art, there is a magnetic recording medium in which a recording layer is formed on a substrate and a protective layer of carbon or the like is formed on the recording layer. The protective layer protects the information recorded on the recording layer and improves the sliding of the magnetic head. However, it is not possible to sufficiently obtain durability of the magnetic recording medium simply by providing a protective layer on the recording layer. For this reason, in general, a lubricant is applied to the surface of the protective layer to form a lubricating layer.

As a lubricant used for forming a lubricating layer of a magnetic recording medium, for example, a lubricant was proposed containing a compound having a polar group such as a hydroxyl group at the end of a fluorine-based polymer having a repeating structure containing $CF_2$ (for example, refer to Patent Documents 1 to 3).

PRIOR ART DOCUMENT

Patent Document

[Patent Document 1] Japanese Patent No. 4632144
[Patent Document 2] Japanese Unexamined Patent Application, First Publication No. 2013-163667
[Patent Document 3] Japanese Patent No. 5613916

SUMMARY OF THE INVENTION

In the magnetic recording/reproducing apparatuses, there is a demand to further reduce the floating height of the magnetic head. For this reason, it is required to further reduce the thickness of the lubricating layer in the magnetic recording medium.

However, when the thickness of the lubricating layer is reduced, the adhesion between the lubricating layer covering the surface of the protective layer and the protective layer is insufficient, and pick-up in which a fluorine-containing ether compound in the lubricating layer adheres to a magnetic head as foreign matter (smears) may occur in some cases.

The present invention has been made in view of the above circumstances, and an object thereof is to provide a fluorine-containing ether compound which can be suitably used as a material of a lubricant for a magnetic recording medium which has good adhesion to a protective layer and which can form a lubricating layer capable of suppressing pick-up.

In addition, another object of the present invention is to provide a lubricant for a magnetic recording medium including the fluorine-containing ether compound of the present invention.

In addition, another object of the present invention is to provide a magnetic recording medium having a lubricating layer using the fluorine-containing ether compound of the present invention.

SUMMARY OF THE INVENTION

The present inventors conducted intensive studies to solve the problems described above.

As a result, it was found that it is sufficient to have a fluorine-containing ether compound in which, at at least one end of a perfluoropolyether (may be referred to below as "PFPE") chain having rigidity, an organic end group is arranged having 3 or more carbon atoms which includes two or more polar groups with each polar group being bonded to different carbon atoms and the carbon atoms to which the polar groups are bonded being bonded to each other via a linking group including the carbon atoms which are not bonded to the polar groups, thereby completing the present invention.

That is, the present invention relates to the following aspects.

[1] A fluorine-containing ether compound according to an aspect of the present invention is represented by Formula (1).

$$R^1-CH_2-R^2-CH_2-R^3 \qquad (1)$$

(In Formula (1), $R^1$ is an organic end group having 3 or more carbon atoms which includes two or more polar groups with each polar group being bonded to different carbon atoms and the carbon atoms to which the polar groups are bonded being bonded to each other via a linking group including the carbon atoms which are not bonded to the polar groups, $R^2$ includes a perfluoropolyether chain represented by Formula (3), and $R^3$ is a hydroxyl group or $R^1$.)

$$-(CF_2)_{y-1}-O-((CF_2)_yO)_z-(CF_2)_{y-1}- \qquad (3)$$

(In Formula (3), y represents an integer of 2 to 4, and z represents an integer of 1 to 30.)

[2] A fluorine-containing ether compound according to another aspect of the present invention is represented by Formula (2).

$$R^1-CH_2-R^2-CH_2-R^1 \qquad (2)$$

(In Formula (2), $R^1$ is an organic end group having 3 or more carbon atoms which includes two or more polar groups with each polar group being bonded to different carbon atoms and the carbon atoms to which the polar groups are bonded being bonded to each other via a linking group including the carbon atoms which are not bonded to the polar groups, and $R^2$ includes a perfluoropolyether chain represented by Formula (3).)

$$-(CF_2)_{y-1}-O-((CF_2)_yO)_z-(CF_2)_{y-1}- \qquad (3)$$

(In Formula (3), y represents an integer of 2 to 4, and z represents an integer of 1 to 30.)

[3] In the fluorine-containing ether compound according to [1] or [2], the polar group included in $R^1$ may be a hydroxyl group.

[4] In the fluorine-containing ether compound according to any one of [1] to [3], $R^1$ may have an ether bond (—O—).

[5] In the fluorine-containing ether compound according to any one of [1] to [4], $R^1$ may be an end group of Formula (4).

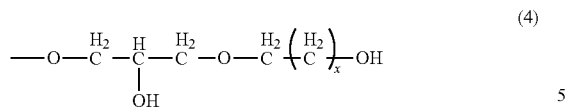

(4)

(In Formula (4), x represents an integer of 1 to 3.)

[6] In the fluorine-containing ether compound according to any one of [1] and [3] to [5], the compound in Formula (1) may be represented by Formula (5).

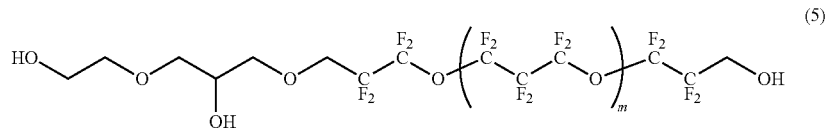

(5)

(In Formula (5), m represents an integer of 1 to 11.)

[7] In the fluorine-containing ether compound according to any one of [1] and [3] to [5], the compound in Formula (1) may be represented by Formula (6).

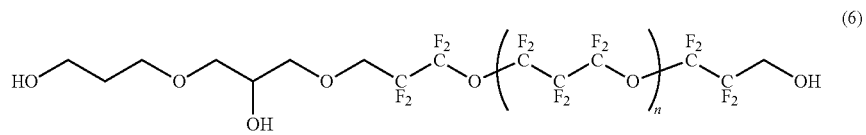

(6)

(In Formula (6), n represents an integer of 1 to 7.)

[8] In the fluorine-containing ether compound according to any one of [1] and [3] to [5], the compound in Formula (1) may be represented by Formula (7).

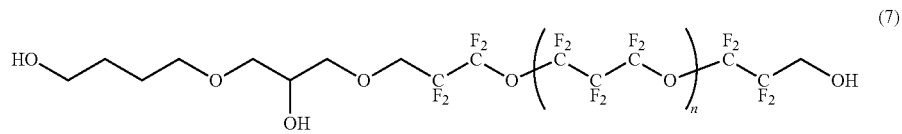

(7)

(In Formula (7), n represents an integer of 1 to 7.)

[9] In the fluorine-containing ether compound according to any one of [2] to [5], the compound in Formula (2) may be represented by Formula (8).

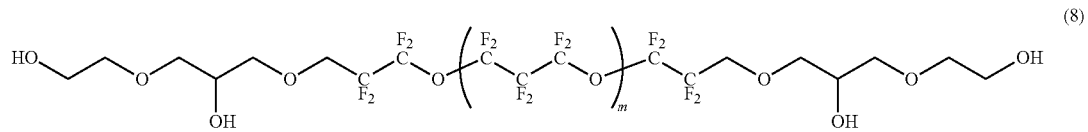

(8)

(In Formula (8), m represents an integer of 1 to 11.)

[10] In the fluorine-containing ether compound according to any one of [2] to [5], the compound in Formula (2) may be represented by Formula (9).

(9)

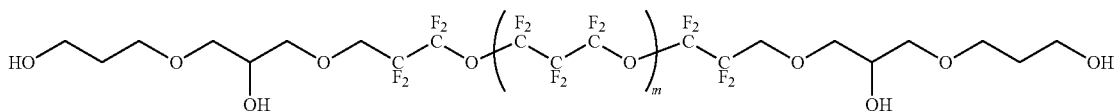

(In Formula (9), n represents an integer of 1 to 7.)

[11] In the fluorine-containing ether compound according to any one of [2] to [5], the compound in Formula (2) may be represented by Formula (10).

(10)

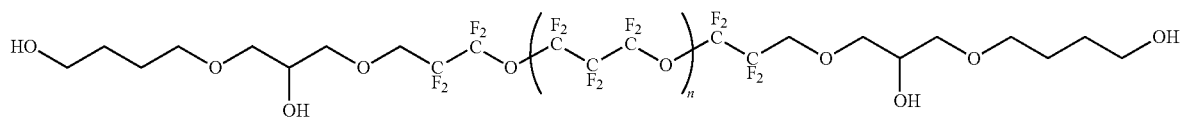

(In Formula (10), n represents an integer of 1 to 7.)

[12] In the fluorine-containing ether compound according to any one of [1] and [3] to [5], the compound in Formula (1) may be represented by Formula (11).

(11)

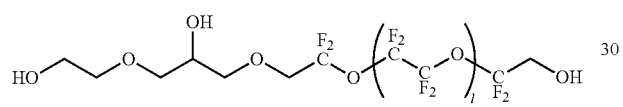

(In Formula (11), l represents an integer of 1 to 15.)

[13] In the fluorine-containing ether compound according to any one of [1] and [3] to [5], the compound in Formula (1) may be represented by Formula (12).

(12)

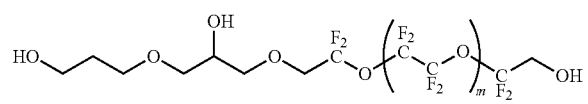

(In Formula (12), m represents an integer of 1 to 11.)

[14] In the fluorine-containing ether compound according to any one of [1] and [3] to [5], the compound in Formula (1) may be represented by Formula (13).

(13)

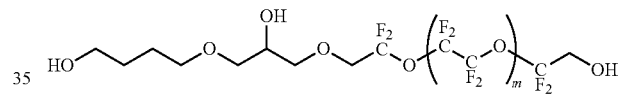

(In Formula (13), m represents an integer of 1 to 11.)

[15] In the fluorine-containing ether compound according to any one of [2] to [5], the compound in Formula (2) may be represented by Formula (14).

(14)

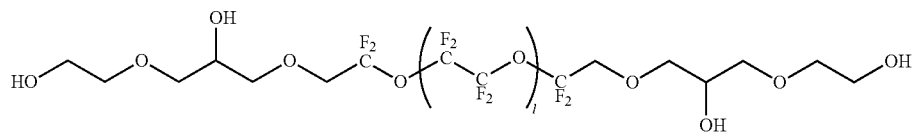

(In Formula (14), l represents an integer of 1 to 15.)

[16] The fluorine-containing ether compound according to any one of [2] to [5], the compound in Formula (2) may be represented by Formula (15).

(15)

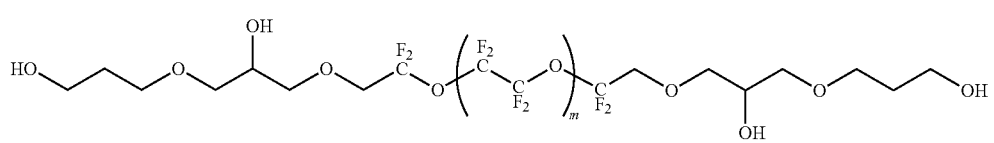

(In Formula (15), m represents an integer of 1 to 11.)

[17] In the fluorine-containing ether compound according to any one of [2] to [5], the compound in Formula (2) may be represented by Formula (16).

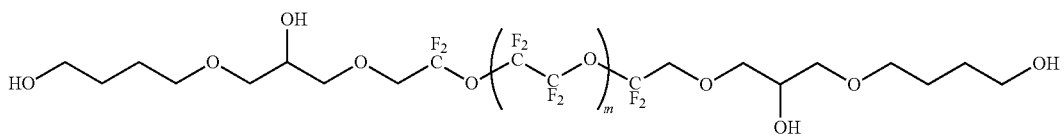

(16)

(In Formula (16), m represents an integer of 1 to 11.)

[18] In the fluorine-containing ether compound according to any one of [1] to [17], a number-average molecular weight may be in a range of 800 to 10,000.

[19] A lubricant for a magnetic recording medium according to another aspect of the present invention includes the fluorine-containing ether compound according to any one of [1] to [18].

[20] A magnetic recording medium according to another aspect of the present invention includes at least a magnetic layer; a protective layer; and a lubricating layer, which are sequentially provided on a substrate, in which the lubricating layer includes the fluorine-containing ether compound according to any one of [1] to [18].

[21] In the magnetic recording medium according to [20], an average film thickness of the lubricating layer may be 0.5 nm to 3 nm.

Effect of the Invention

The fluorine-containing ether compound of the present invention is a compound represented by Formula (1) and is suitable as a material for a lubricant for a magnetic recording medium.

Since the lubricant for a magnetic recording medium of the present invention includes the fluorine-containing ether compound of the present invention, it is possible to form a lubricating layer having good adhesion to the protective layer and capable of suppressing pick-up.

Since the magnetic recording medium of the present invention has a lubricating layer having good adhesion to the protective layer and capable of suppressing pick-up, the durability thereof is excellent.

BRIEF DESCRIPTION OF THE DRAWINGS

FIG. 1 is a schematic cross-sectional view showing one embodiment of a magnetic recording medium of the present invention.

DETAILED DESCRIPTION OF THE INVENTION

A detailed description will be given below of the fluorine-containing ether compound, the lubricant for a magnetic recording medium, and the magnetic recording medium of the present invention. The present invention is not limited only to the embodiments described below.

[Fluorine-Containing Ether Compound]

The fluorine-containing ether compound of the present embodiment is represented by Formula (1).

$R^1—CH_2—R^2—CH_2—R^3$ (1)

(In Formula (1), $R^1$ is an organic end group having 3 or more carbon atoms which includes two or more polar groups with each polar group being bonded to different carbon atoms and the carbon atoms to which the polar groups are bonded being bonded to each other via a linking group including the carbon atoms which are not bonded to the polar groups, $R^2$ includes a perfluoropolyether chain represented by Formula (3), and $R^3$ is a hydroxyl group or $R^1$.)

$—(CF_2)_{y-1}—O—((CF_2)_yO)_z—(CF_2)_{y-1}—$ (3)

(In Formula (3), y represents an integer of 2 to 4, and z represents an integer of 1 to 30.)

Here, description will be given of the reasons why the lubricating layer can cover the surface of the protective layer with a high coverage ratio and has excellent adhesion to the protective layer in a case where a lubricating layer is formed on the protective layer of the magnetic recording medium using a lubricant for a magnetic recording medium including the fluorine-containing ether compound of the present embodiment (may be abbreviated below as "lubricant").

As shown in Formula (1), in the fluorine-containing ether compound of the present embodiment, the end group represented by $R^1$ is arranged at one end of a perfluoropolyether chain represented by $R^2$ (may be abbreviated below as "PFPE chain"), and the end group represented by $R^3$ is arranged at the other end. In the lubricating layer including the fluorine-containing ether compound of the present embodiment, the two or more polar groups included in the end group represented by $R^1$ bring the fluorine-containing ether compound and the protective layer into tight contact with each other. In the lubricating layer including the fluorine-containing ether compound of the present embodiment, the PFPE chain represented by $R^2$ covers the surface of the protective layer and reduces the frictional force between the magnetic head and the protective layer. Furthermore, in the lubricating layer including the fluorine-containing ether compound of the present embodiment, $R^2$ including the PFPE chain represented by Formula (3) is adhered (adsorbed) to the protective layer by the polar groups of $R^1$ and $R^3$. Formula (3) has a repeating unit having rigidity formed of a linear fluorinated alkyl ether group. Therefore, it is possible for the PFPE chain to form a loop structure on the protective layer. As a result, the lubricating layer has good adhesion to the protective layer.

In addition, two or more polar groups included in the end group represented by $R^1$ are bonded to different carbon atoms, the carbon atoms to which the polar groups are bonded being bonded to each other via a linking group including the carbon atoms which are not bonded to the polar groups. The fluorine-containing ether compound having an end group represented by $R^1$ does not easily aggregate, for example, compared with a fluorine ether compound having end groups in which carbon atoms to which polar groups are bonded are bonded to each other. Therefore, in the lubricating layer including the fluorine-containing ether compound of the present embodiment, it is possible to prevent the fluorine-containing ether compound present without being adhered (adsorbed) to the protective layer from aggregating and adhering to the magnetic head as foreign matter (smears), and pick-up is suppressed. In addition, since the fluorine-containing ether compounds do not easily aggregate to each other, the fluorine-containing ether compound in the lubricating layer is easily arranged in a state where the fluorine-containing ether compound spreads and extends in the planar direction on the protective layer. Thus, using the lubricant including the fluorine-containing ether compound described above makes it possible to form a lubricating layer which can coat the surface of the protective layer with a high coverage ratio and which has good wear resistance even when the thickness is reduced.

In addition, in the end group represented by $R^1$, the carbon atoms to which the polar groups are bonded are bonded to each other via a linking group including the carbon atom to which the polar group is not bonded. Therefore, in a case where the protective layer on which the lubricant is coated is formed of carbon or carbon including nitrogen, two or more polar groups of $R^1$ tend to be oriented in the same direction with respect to the surface of the protective layer, resulting in a three-dimensional arrangement in which the polar groups tend to adhere to the protective layer surface. Accordingly, in the lubricating layer including the fluorine-containing ether compound of the present embodiment, in particular, in a case where the protective layer is formed of carbon or carbon including nitrogen, the adhesion to the protective layer is further improved.

In the fluorine-containing ether compound represented by Formula (1), $R^1$ is an organic end group having 3 or more carbon atoms which includes two or more polar groups with each polar group being bonded to different carbon atoms and the carbon atoms to which the polar groups are bonded being bonded to each other via a linking group including the carbon atoms which are not bonded to the polar groups.

It is possible to appropriately select $R^1$ in Formula (1) according to the performance required for a lubricant including a fluorine-containing ether compound.

Examples of the polar group in $R^1$ include a hydroxyl group, a carboxyl group, an amino group, an aminocarboxyl group, and the like. The polar group in $R^1$ is preferably a hydroxyl group since it is possible to obtain a lubricating layer including a fluorine-containing ether compound having good adhesion to the protective layer. Here, the ether bond (—O—) is not included in the polar group in $R^1$.

The number of polar groups in $R^1$ is 2 or more, and preferably 2 to 4. When the number of polar groups in $R^1$ is large, the polar groups are less likely to be oriented with the surface of the protective layer due to steric hindrance. Therefore, the number of polar groups in $R^1$ is most preferably two.

Two or more polar groups in $R^1$ may all be different from each other, or some or all may be the same.

The linking group in $R^1$ is not particularly limited, and can be appropriately selected according to the performance required for a lubricant including a fluorine-containing ether compound. Specifically, examples thereof include an alkylene group having 1 to 4 carbon atoms such as a methylene group, an ethylene group, and a propylene group. These alkylene groups may be linked via an ether bond.

$R^1$ preferably has an ether bond (—O—). The ether bond in $R^1$ is preferably included in the linking group.

$R^1$ is preferably an end group represented by Formula (4). The end group represented by Formula (4) contributes to improvement in adhesion between the protective layer on which the lubricant containing the fluorine-containing ether compound of this embodiment is coated and the lubricating layer formed by coating the lubricant.

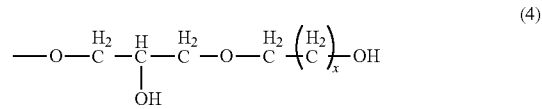

(In Formula (4), x represents an integer of 1 to 3.)

In Formula (4), in a case where x is an integer of 1 to 3, the distance between the hydroxyl group on the $R^2$ side in Formula (4) and the end hydroxyl group is appropriate. As a result, it is possible to form a lubricating layer which generates foreign matter (smears) less easily.

In the fluorine-containing ether compound represented by Formula (1), $R^3$ is a hydroxyl group or $R^1$.

In a case where $R^1$ is a hydroxyl group, similarly to the end hydroxyl group of Formula (4), adhesion is obtained due to hydrogen bonding with the protective layer to be coated with a lubricant including a fluorine-containing ether compound, which is preferable.

In a case where $R^3$ is $R^1$, adhesion between the protective layer coated with the lubricant including the fluorine-containing ether compound and the lubricating layer formed by coating the lubricant is further improved, which is preferable. In a case where $R^3$ is $R^1$, $R^3$ and $R^1$ in the fluorine-containing ether compound represented by Formula (1) may be the same as each other as represented by Formula (2) or different from each other.

It is possible to appropriately select $R^3$ in Formula (1) according to the performance required for a lubricant including a fluorine-containing ether compound.

$$R^1\text{—}CH_2\text{—}R^2\text{—}CH_2\text{—}R^1 \qquad (2)$$

(In Formula (2), $R^1$ is an organic end group having 3 or more carbon atoms which includes two or more polar groups with each polar group being bonded to different carbon atoms and the carbon atoms to which the polar groups are bonded being bonded to each other via a linking group including the carbon atoms which are not bonded to the polar groups and $R^2$ includes a perfluoropolyether chain represented by Formula (3)).

(In Formula (3), y represents an integer of 2 to 4, and z represents an integer of 1 to 30.)

In Formulas (1) and (2), $R^2$ includes a perfluoropolyether chain (PFPE chain) represented by Formula (3). In a case where the lubricant including the fluorine-containing ether compound is coated on the protective layer to form the lubricating layer, the PFPE chain represented by Formula (3) covers the surface of the protective layer and imparts lubrication to the lubricating layer to reduce the frictional force between the magnetic head and the protective layer. In addition, the PFPE chain represented by Formula (3) has high rigidity in comparison with, for example, a PFPE chain including a repeating unit formed of a PFPE chain other than that represented by Formula (3). Therefore, the fluorine-containing ether compound of the present embodiment has high rigidity in the main chain.

(In Formula (3), y represents an integer of 2 to 4, and z represents an integer of 1 to 30.)

In Formula (3), y is an integer of 2 to 4, and z is an integer of 1 to 30. In Formula (3), y is preferably an integer of 2 to 3. In Formula (3), z is preferably an integer of 1 to 20, and more preferably an integer of 1 to 15.

In the present embodiment, since y in Formula (3) is an integer of 2 to 4 and z is an integer of 1 to 30, the number-average molecular weight of the fluorine-containing ether compound is in a preferable range. In addition, since y in Formula (3) is an integer of 2 to 4 and z is an integer of 1 to 30, the ratio of the number of oxygen atoms (the number of ether bonds (—O—)) to the number of carbon atoms in the PFPE chain is appropriate and a fluorine-containing ether compound having appropriate rigidity is obtained. In addition, since y in Formula. (3) is an integer of 2 to 4 and z is an integer of 1 to 30, the orientation of the polar group in the fluorine-containing ether compound coated on the protective layer is easily held due to the rigidity in the PFPE chain, and the fluorine-containing ether compound does not easily aggregate on the protective layer. As a result, it is possible to form a lubricating layer having a small thickness on the protective layer with a sufficient coverage ratio using the fluorine-containing ether compound. In addition, it is possible for the PFPE chain to form a loop structure on the protective layer using the fluorine-containing ether compound.

Specifically, the fluorine-containing ether compound of the present embodiment is preferably any one of compounds represented by Formulas (5) to (20).

However, each numerical value of l, m, and n in each formula signifies any one of the integer values in the numerical range. For example, in the compound represented by Formula (17), n represents any one of 1, 2, 3, . . . , 7. Accordingly, in the ranges shown by the compound represented by Formula (17), the compound is at least one compound in which n is 1 to 7, and is not a compound representing a mixture formed of all of the compounds in which n is 1 to 7. The same applies to other formulas.

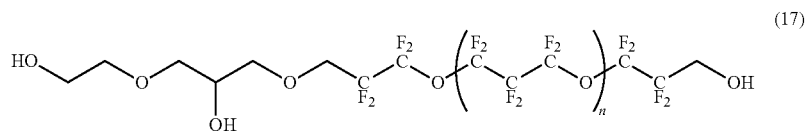

(17)

(In Formula (17), n represents an integer of 1 to 7.)

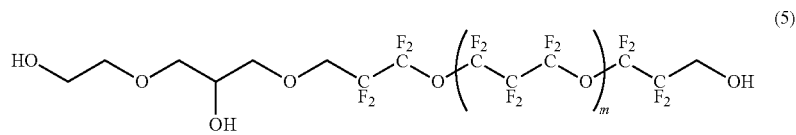

(5)

(In Formula (5), m represents an integer of 1 to 11.)

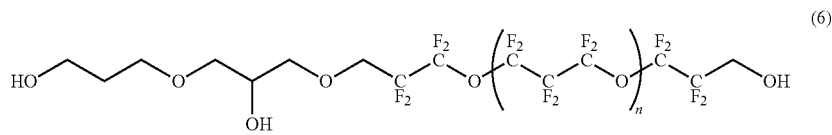

(6)

(In Formula (6), n represents an integer of 1 to 7.)

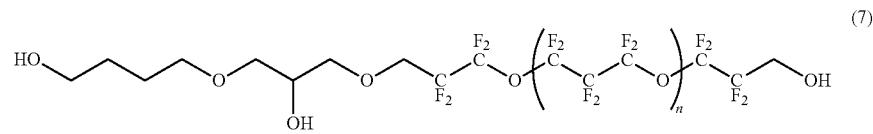

(7)

(In Formula (7), n represents an integer of 1 to 7.)

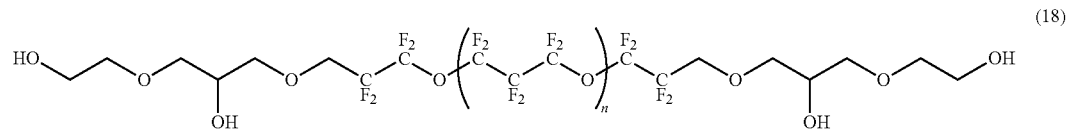

(18)

(In Formula (18), n represents an integer of 1 to 7.)

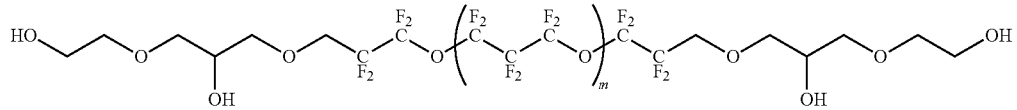
(8)
(In Formula (8), m represents an integer of 1 to 1.)
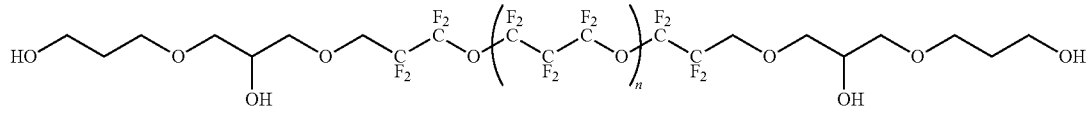
(9)
(In Formula (9), n represents an integer of 1 to 7.)
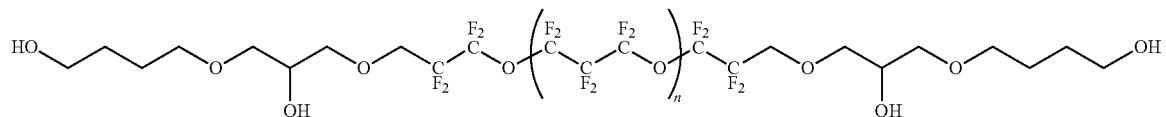
(10)
(In Formula (10), n represents an integer of 1 to 7.)
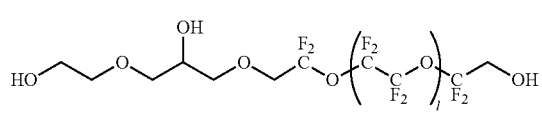
(19)
(In Formula (19), m represents an integer of 1 to 11.)
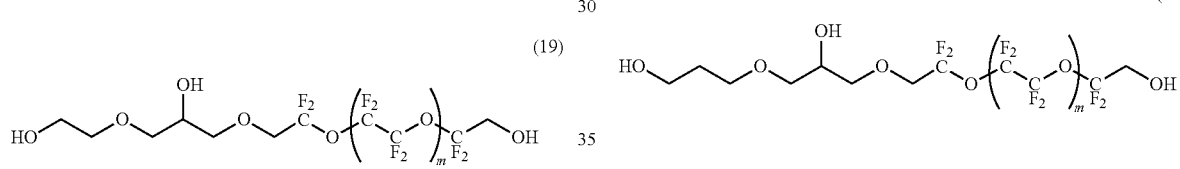
(12)
(In Formula (12), m represents an integer of 1 to 11.)
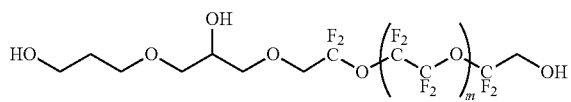
(11)
(In Formula (11), l represents an integer of 1 to 15.)
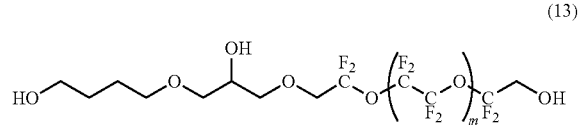
(13)
(In Formula (13), m represents an integer of 1 to 1.)
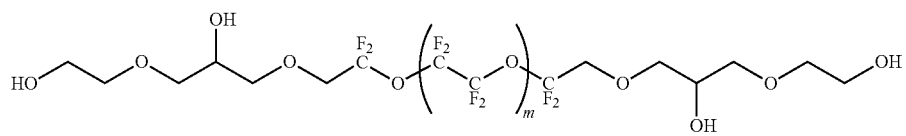
(20)
(In Formula (20), m represents an integer of 1 to 11)
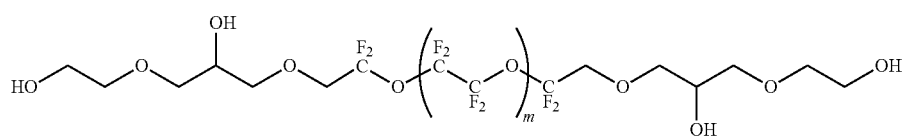
(14)
(In Formula (14), l represents an integer of 1 to 15.)

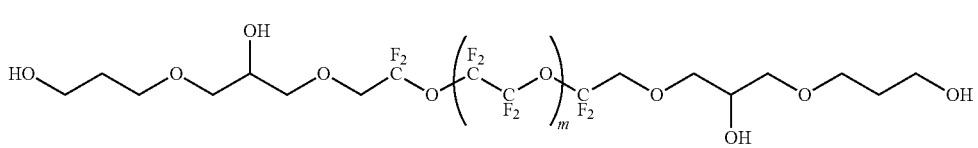

(15)

(In Formula (15), m represents an integer of 1 to 11.)

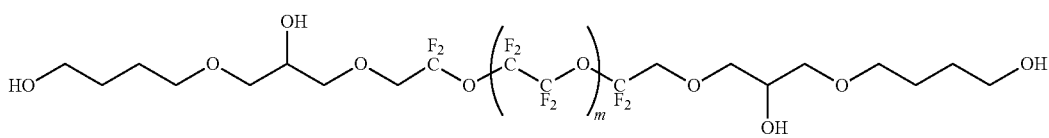

(16)

(In Formula (16), m represents an integer of 1 to 11.)

In a case where the fluorine-containing ether compound represented by Formula (1) is any one of the compounds represented by Formulas (5) to (20), it is possible to form a lubricating layer in which the adhesion with the protective layer is further improved and pick-up is suppressed, which is preferable.

Among the fluorine-containing ether compounds represented by Formulas (5) to (20), in particular, the fluorine-containing ether compounds represented by Formulas (8) to (10), (14) to (16), (18), and (20), which are fluorine-containing ether compounds represented by Formula (2), can form a lubricating layer having good adhesion to the protective layer, which is preferable.

The fluorine-containing ether compound of the present embodiment preferably has a number-average molecular weight within the range of 800 to 10,000. When the number-average molecular weight is 800 or more, the lubricant including the fluorine-containing ether compound of the present embodiment does not easily evaporate and it is possible to prevent the lubricant evaporating and being transferred to the magnetic head. The number-average molecular weight of the fluorine-containing ether compound is more preferably 1,000 or more. In addition, when the number-average molecular weight is 10,000 or less, the viscosity of the fluorine-containing ether compound is appropriate and it is possible to easily form a lubricating layer having a small thickness by coating a lubricant including the fluorine-containing ether compound. The number-average molecular weight of the fluorine-containing ether compound is preferably 4,000 or less such that the viscosity allows easy handling in a case of being applied to a lubricant.

The number-average molecular weight is a value measured by $^{1}$H-NMR and $^{19}$F-NMR by AVANCE III 400 manufactured by Bruker BioSpin Co., Ltd. In the nuclear magnetic resonance (NMR) measurement, the sample was diluted in a hexafluorobenzene/d-acetone (1/4 (v/v)) solvent and used for the measurement. The basis of the $^{19}$F-NMR chemical shift was set to a peak of hexafluorobenzene at −164.7 ppm, and the basis of the $^{1}$H-NMR chemical shift was set to a peak of acetone at 2.2 ppm.

[Manufacturing Method]

The method for manufacturing the fluorine-containing ether compound of the present embodiment is not particularly limited, and manufacturing is possible by a manufacturing method known in the related art. It is possible to manufacture the fluorine-containing ether compound of the present embodiment, for example, using the manufacturing method described below.

First, a fluorine compound having hydroxymethyl groups (—CH$_2$OH) arranged at both ends of a perfluoropolyether chain corresponding to R$^2$ in Formula (1) is prepared.

Subsequently, the hydroxyl group of the hydroxymethyl group arranged at both ends (or one end) of the fluorine compound is substituted with a compound having an organic end group formed of R$^1$ in Formula (1). In a case of manufacturing a fluorine-containing ether compound in which R$^3$ is a hydroxyl group as the fluorine-containing ether compound, at the time of the substitution reaction described above, the compound having an organic end group formed of R$^1$ is used in an amount of 1 equivalent with respect to the perfluoropolyether chain. In addition, in a case of manufacturing a fluorine-containing ether compound in which R$^3$ is R$^3$ as a fluorine-containing ether compound, at the time of the substitution reaction described above, the compound having an organic end group formed of R$^1$ is used in an amount of 2 equivalents or more with respect to the perfluoropolyether chain. It is possible to perform these substitution reactions by a method known in the related art and it is possible to appropriately determine the method according to the types of R$^1$ and R$^3$ in Formula (1). The compound represented by Formula (1) is obtained by the above method.

The fluorine-containing ether compound of the present embodiment is a compound represented by Formula (1). Accordingly, when a lubricating layer is formed on the protective layer using the lubricant containing the fluorine-containing ether compound, the surface of the protective layer is covered with the PFPE chain represented by R$^2$ in Formula (1), and the frictional force between the magnetic head and the protective layer is reduced. In addition, excellent wear resistance is obtained in the lubricating layer formed using the lubricant including the fluorine-containing ether compound of the present embodiment due to the intermolecular interaction among two or more hydroxyl groups of the organic end group represented by R$^1$.

In addition, in the fluorine-containing ether compound of the present embodiment, the PFPE chain is adhered on the protective layer by bonding between the protective layer and two or more polar groups of the organic end group represented by R, linked to the PFPE chain. Accordingly, the lubricating layer and the protective layer are tightly bonded, and pick-up is suppressed.

[Lubricant for Magnetic Recording Medium]

The lubricant for a magnetic recording medium of the present embodiment includes a fluorine-containing ether compound represented by Formula (I).

As long as the lubricant of the present embodiment is in a range which does not impair characteristics due to the inclusion of the fluorine-containing ether compound represented by Formula (1), it is possible to use known materials for a lubricant in a mixture as necessary.

Specific examples of known materials include FOMBLIN (registered trademark) ZDIAC, FOMBLIN ZDEAL, FOMBLIN AM-2001 (manufactured by Solvay Solexis Inc.), Moresco A 20 H (manufactured by Moresco Corp.), and the like.

A known material used by mixing with the lubricant of the present embodiment preferably has a number-average molecular weight of 1,000 to 10,000.

In the case where the lubricant of the present embodiment includes another material of the fluorine-containing ether compound represented by Formula (1), the content of the fluorine-containing ether compound represented by Formula (1) in the lubricant of the present embodiment is preferably 50% by mass or more, and more preferably 70% by mass or more.

Since the lubricant of the present embodiment includes the fluorine-containing ether compound represented by Formula (1), even if the thickness is reduced, it is possible to cover the surface of the protective layer with a high coverage ratio, and it is possible to form a lubricating layer with excellent adhesion to the protective layer. In addition, since the lubricant of the present embodiment includes the fluorine-containing ether compound represented by Formula (1), the fluorine-containing ether compound in the lubricating layer which is present without being adhered (adsorbed) to the protective layer does not easily aggregate. Thus, it is possible to prevent the fluorine-containing ether compound from aggregating and adhering to the magnetic head as foreign matter (smears), thereby suppressing pick-up.

[Magnetic Recording Medium]

FIG. 1 is a schematic cross-sectional view showing one embodiment of the magnetic recording medium of the present invention.

The magnetic recording medium 10 of the present embodiment has a structure in which an adhesive layer 12, a soft magnetic layer 13, a first underlayer 14, a second underlayer 15, a magnetic layer 16, a protective layer 17, and a lubricating layer 18 are sequentially provided on a substrate 11.

[Substrate]

As the substrate 11, for example, it is possible to use a nonmagnetic substrate or the like in which a layer formed of NiP or NiP alloy is formed on a substrate formed of a metal or an alloy material such as Al or an Al alloy.

In addition, as the substrate 11, a nonmagnetic substrate formed of a non-metallic material such as glass, ceramics, silicon, silicon carbide, carbon, resin, or the like may be used, or a nonmagnetic substrate in which a layer of an NiP or NiP alloy is formed on a base formed of these non-metal materials may be used.

[Adhesive Layer]

The adhesive layer 12 prevents the progress of corrosion of the substrate 11 in a case where the substrate 11 and the soft magnetic layer 13 provided on the adhesive layer 12 are arranged in contact with each other.

It is possible to appropriately select the material of the adhesive layer 12 from, for example, Cr, a Cr alloy, Ti, a Ti alloy, and the like. It is possible to form the adhesive layer 12 by, for example, a sputtering method.

[Soft Magnetic Layer]

It is preferable that the soft magnetic layer 13 have a structure in which a first soft magnetic layer, an intermediate layer formed of a Ru layer, and a second soft magnetic layer are laminated in order, That is, the soft magnetic layer 13 preferably has a structure in which, by interposing an intermediate layer formed of a Ru layer between two layers of soft magnetic layers, the upper and lower soft magnetic layers of the intermediate layer are bonded by anti-ferrocoupling (AFC). When the soft magnetic layer 13 has an AFC-bonded structure, it is possible to increase the resistance to external magnetic fields and the resistance to the Wide Area Tack Erasure (WATE) phenomenon, which is a problem peculiar to perpendicular magnetic recording.

It is preferable that the first soft magnetic layer and the second soft magnetic layer be layers formed of a CoFe alloy. In a case where the first soft magnetic layer and the second soft magnetic layer are layers formed of a CoFe alloy, it is possible to realize a high saturation magnetic flux density Bs (1.4 (T) or more).

In addition, it is preferable to add any one of Zr, Ta, or Nb to the CoFe alloy used for the first soft magnetic layer and the second soft magnetic layer. Due to this, amorphization of the first soft magnetic layer and the second soft magnetic layer is promoted, and it is possible to improve the orientation of the first underlayer (seed layer), and it is also possible to reduce the floating height of the magnetic head.

It is possible to form the soft magnetic layer 13 by, for example, a sputtering method.

[First Underlayer]

The first underlayer 14 is a layer for controlling the orientation and crystal size of the second underlayer 15 and the magnetic layer 16 provided thereon. The first underlayer 14 is provided to increase the components in the direction perpendicular to the substrate surface of the magnetic flux generated from the magnetic head and fix the magnetization direction of the magnetic layer 16 more firmly in the direction perpendicular to the substrate 11.

The first underlayer 14 is preferably a layer formed of a NiW alloy. In the case where the first underlayer 14 is a layer formed of a NiW alloy, other elements such as B, Mn, Ru, Pt, Mo, Ta and the like may be added to the NiW alloy as necessary.

It is possible to form the first underlayer 14 by, for example, a sputtering method.

[Second Underlayer]

The second underlayer 15 is a layer which controls the orientation of the magnetic layer 16 so as to be favorable. The second underlayer 15 is preferably a layer formed of Ru or a Ru alloy.

The second underlayer 15 may be a layer formed of one layer or a plurality of layers. In the case where the second underlayer 15 is formed of a plurality of layers, all of the layers may be formed of the same material, or at least one layer may be formed of a different material.

It is possible to form the second underlayer 15 by, for example, a sputtering method.

[Magnetic Layer]

The magnetic layer 16 is formed of a magnetic layer in which the axis of easy magnetization is perpendicular or horizontal to the substrate surface. The magnetic layer 16 is a layer including Co and Pt and may be a layer including an oxide or Cr, B, Cu, Ta, Zr or the like in order to further improve the SNR characteristics.

Examples of the oxide contained in the magnetic layer 16 include $SiO_2$, SiO, $Cr_2O_3$, CoO, $Ta_2O_3$, $TiO_2$, and the like.

The magnetic layer 16 may be formed of one layer or formed of a plurality of magnetic layers formed of materials having different compositions.

For example, in the case where the magnetic layer 16 is formed of three layers of a first magnetic layer, a second magnetic layer, and a third magnetic layer, the first magnetic layer includes Co, Cr, and Pt, and preferably has a granular structure formed of a material including an oxide. As the oxide contained in the first magnetic layer, for example, it is preferable to use oxides such as Cr, Si, Ta, Al, Ti, Mg, and Co. Among these, in particular, it is possible to suitably use $TiO_2$, $Cr_2O_3$, $SiO_2$, and the like. In addition, the first magnetic layer is preferably formed of a composite oxide to which two or more oxides are added. Among these, it is possible to preferably use $Cr_2O_3$—$SiO_2$, $Cr_2O_3$—$TiO_2$, $SiO_2$—$TiO_2$, and the like.

In addition to Co, Cr, Pt and an oxide, the first magnetic layer is able to include one or more elements selected from B, Ta, Mo, Cu, Nd, W, Nb, Sm, Tb, Ru, and Re. By including one or more of the above elements, it is possible to promote miniaturization of the magnetic particles, to improve crystallinity and orientation, and to obtain recording/reproduction characteristics and thermal fluctuation characteristics suitable for higher density recording.

For the second magnetic layer, it is possible to use the same material as the first magnetic layer. It is preferable that the second magnetic layer have a granular structure.

The third magnetic layer preferably has a non-granular structure formed of a material which includes Co, Cr, and Pt and which does not include oxide. In addition to Co, Cr, and Pt, it is possible for the third magnetic layer to include one or more elements selected from B, Ta, Mo, Cu, Nd, W, Nb, Sm, Tb, Ru, Re, and Mn. Including the above elements in addition to Co, Cr and Pt in the third magnetic layer makes it possible to promote miniaturization of the magnetic particles, to improve crystallinity and orientation, and to obtain recording and reproduction characteristics and thermal fluctuation characteristics suitable for higher density recording.

In the case where the magnetic layer 16 is formed of a plurality of magnetic layers, it is preferable to provide a nonmagnetic layer between the adjacent magnetic layers. In a case where the magnetic layer 16 is formed of three layers of the first magnetic layer, the second magnetic layer, and the third magnetic layer, it is preferable to provide a nonmagnetic layer between the first magnetic layer and the second magnetic layer and between the second magnetic layer and the third magnetic layer.

By providing the nonmagnetic layer with an appropriate thickness between the adjacent magnetic layers, the magnetization reversal of each layer is facilitated, it is possible to reduce the dispersion of the magnetization reversal of the whole magnetic particles, and it is possible to further improve the S/N ratio.

For the nonmagnetic layer provided between the adjacent magnetic layers of the magnetic layer 16, it is possible to suitably use, for example, Ru, Ru alloy, CoCr alloy, CoCrX1 alloy (X1 represents one or two or more elements selected from Pt, Ta, Re, Ru, Cu, Nb, Ni, Mn, Ge, Si, O, N, W, Mo, Ti, V, Zr, and B) or the like.

It is preferable to use an alloy material including an oxide, a metal nitride, or a metal carbide for the nonmagnetic layer provided between the adjacent magnetic layers of the magnetic layer 16. Specifically, as the oxide, for example, it is possible to use $SiO_2$, $Al_2O_3$, $Ta_2O_5$, $Cr_2O_3$, MgO, $Y_2O_3$, $TiO_2$, or the like. As the metal nitride, for example, it is possible to use AlN, $Si_3N_4$, TaN, CrN, or the like. As the metal carbide, for example, it is possible to use TaC, BC, SiC, or the like.

It is possible to form the nonmagnetic layer by, for example, a sputtering method.

In order to realize a higher recording density, the magnetic layer 16 is preferably a perpendicular magnetic recording magnetic layer whose easy axis of magnetization is oriented perpendicular to the substrate surface. The magnetic layer 16 may be for in-plane magnetic recording.

The magnetic layer 16 may be formed by any method known in the related art, such as a vapor deposition method, an ion beam sputtering method, a magnetron sputtering method, or the like. The magnetic layer 16 is usually formed by a sputtering method.

[Protective Layer]

The protective layer 17 protects the magnetic layer 16. The protective layer 17 may be formed of one layer or may be formed of a plurality of layers. Examples of the material of the protective layer 17 include carbon, carbon including nitrogen, silicon carbide, and the like.

As a method for layer-forming the protective layer 17, it is possible to use a sputtering method using a target material including carbon, a chemical vapor deposition (CVD) method using a hydrocarbon material such as ethylene or toluene, an ion beam deposition (IBD) method, or the like.

[Lubricating Layer]

The lubricating layer 18 prevents contamination of the magnetic recording medium 10. In addition, the lubricating layer 18 improves the durability of the magnetic recording medium 10 by reducing the frictional force of the magnetic head of the magnetic recording/reproducing apparatus sliding on the magnetic recording medium 10.

As shown in FIG. 1, the lubricating layer 18 is formed in contact with the protective layer 17. The lubricating layer 18 is formed by coating the lubricant for the magnetic recording medium of the embodiment described above on the protective layer 17. Therefore, the lubricating layer 18 includes the fluorine-containing ether compound described above.

In the case where the protective layer 17 arranged under the lubricating layer 18 is formed of carbon, carbon including nitrogen, or silicon carbide, the lubricating layer 18 is bonded with a high bonding force with the fluorine-containing ether compound included in the lubricating layer 18. As a result, even if the thickness of the lubricating layer 18 is reduced, it is easy to obtain the magnetic recording medium 10 in which the surface of the protective layer 17 is covered with a high coverage ratio, and it is possible to effectively prevent contamination of the surface of the magnetic recording medium 10.

The average film thickness of the lubricating layer 18 is preferably 0.5 nm (5 Å) to 3 nm (30 Å), more preferably 0.5 nm (5 Å) to 2 nm (20 Å).

When the average film thickness of the lubricating layer 18 is 0.5 nm or more, the lubricating layer 18 is formed with a uniform film thickness without being formed into an island shape or mesh shape. Therefore, it is possible for the lubricating layer 18 to cover the surface of the protective layer 17 with a high coverage ratio. In addition, setting the average film thickness of the lubricating layer 18 to 3 nm or less makes it possible to make the floating height of the magnetic head sufficiently small, and to increase the recording density of the magnetic recording medium 10.

In the case where the surface of the protective layer 17 is not covered with the lubricating layer 18 at a sufficiently high coverage ratio, environmental substances adsorbed on the surface of the magnetic recording medium 10 pass through the gap of the lubricating layer 18, and permeate under the lubricating layer 18. The environmental substances which permeated the lower layer of the lubricating layer 18 adsorb to and bond with the protective layer 17 to generate contaminants. Then, at the time of magnetic recording/reproduction, these contaminants (aggregated components) adhere (transfer) to the magnetic head as a smear, which damages the magnetic head and deteriorates the magnetic recording/reproducing characteristics of the magnetic recording/reproducing apparatus.

Examples of environmental substances which generate contaminants include hydrocarbons having relatively high molecular weights such as siloxane compounds (cyclic siloxanes and linear siloxanes), ionic impurities and octacosane, plasticizers such as dioctyl phthalate, and the like. Examples of the metal ions included in the ionic impurities include sodium ions, potassium ions, and the like. Examples of inorganic ions included in the ionic impurities include chlorine ions, bromine ions, nitrate ions, sulfate ions, ammonium ions, and the like. Examples of organic ions included in the ionic impurities include oxalic acid ions, formic acid ions, and the like.

[Method of Forming Lubricating Layer]

In order to form the lubricating layer 18, example methods include a method of preparing a magnetic recording medium in the manufacturing process of forming each layer up to the protective layer 17 on the substrate 11, and coating the lubricating layer-forming solution on the protective layer 17.

The lubricating layer-forming solution is obtained by diluting the lubricant for a magnetic recording medium of the embodiment described above with a solvent as necessary and setting a viscosity and a concentration suitable for the coating method. Examples of a solvent to be used for the lubricating layer-forming solution include a fluorine-based solvent such as Vertrel (registered trademark) XF (trade name, manufactured by Du Pont-Mitsui Fluorochemicals Co., Ltd.), and the like.

The method of coating the lubricating layer-forming solution is not particularly limited, and examples thereof include a spin coating method and a dipping method. In the case of using the dipping method, for example, it is possible to use the following method. First, the substrate 11 on which each layer up to the protective layer 17 is formed is immersed in a lubricating layer-forming solution placed in an immersion tank of a dip coating apparatus. Next, the substrate 11 is pulled up from the immersion tank at a predetermined speed. Due to this, the lubricating layer-forming solution is coated on the surface of the protective layer 17 on the substrate 11.

Using the dipping method, it is possible to uniformly coat the lubricating layer-forming solution on the surface of the protective layer 17, and to form the lubricating layer 18 with a uniform film thickness on the protective layer 17.

In the magnetic recording medium 10 of the present embodiment, at least a magnetic layer 16, a protective layer 17, and a lubricating layer 18 are sequentially provided on a substrate 11. In the magnetic recording medium 10 of the present embodiment, a lubricating layer 18 including the fluorine-containing ether compound described above is formed in contact on the protective layer 17. Even if the thickness is reduced, the lubricating layer 18 covers the surface of the protective layer 17 with a high coverage ratio. Thus, in the magnetic recording medium 10 of the present embodiment, environmental substances which generate contaminants such as ionic impurities are prevented from entering the gaps of the lubricating layer 18. Accordingly, the magnetic recording medium 10 of the present embodiment has few contaminants present on the surface. In addition, the lubricating layer 18 in the magnetic recording medium 10 of the present embodiment is less likely to produce foreign matter (smears) and it is possible to suppress pick-up. In addition, the lubricating layer 18 in the magnetic recording medium 10 of the present embodiment has excellent wear resistance.

EXAMPLES

A more detailed description will be given below of the present invention with reference to Examples and Comparative Examples. Here, the present invention is not limited to only the following examples.

Example 1

In a nitrogen atmosphere, a fluoropolyether (mixture where $n^1$=1 to 7, number-average molecular weight 1,280, molecular weight distribution 1.2) represented by $HOCH_2CF_2CF_2O(CF_2CF_2CF_2O)_n{}^1CF_2CF_2CH_2OH$ (10 g), t-butanol (70 mL), and potassium tert-butoxide (0.9 g) were placed into a 300 mL eggplant-shaped flask to form a mixture. The obtained mixture was stirred for 1 hour while being heated to 70° C.

Next, epibromohydrin (3.1 g) was added dropwise to the mixture described above, and the mixture was further stirred for 5 hours while being heated to 70° C. and cooled to 25° C. Thereafter, the reaction product described above was washed with water by adding a fluorine-based solvent (trade name: ASAHIKLIN (registered trademark) AK-225, manufactured by Asahi Glass Co., Ltd.) to the eggplant-shaped flask described above, and the organic phase in the eggplant-shaped flask was recovered. Subsequently, sodium sulfate was added to the recovered organic phase and dehydrated, and then filter filtration was performed. Subsequently, the solvent was distilled off from the filtrate using an evaporator Thereafter, the residue was separated by column chromatography.

A colorless and transparent liquid compound 1 (5.0 g) represented by Formula (A) was obtained by the above steps.

$^1$H-NMR and $^{19}$F-NMR measurement of the obtained compound 1 was performed and the structure was identified based on the following results.

$^1$H-NMR (acetone-$D_6$): δ [ppm]=2.60 (1H), 2.77 (1H), 3.12 (1H), 3.57 (1H), 3.95 (1H), 4.00 (2H), 4.12 (2H)

$^{19}$F-NMR (acetone-$D_6$): δ [ppm]=−130.00 to −129.00 (12F), −127.48 (2F), −124.33 (2F), −86.42 (4F), −84.00 to −83.00 (24F)

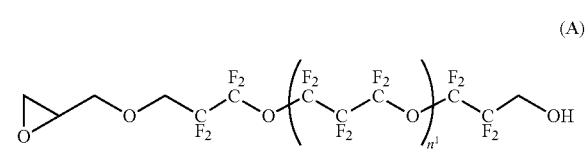

(A)

(In Formula (A), $n^1$ represents an integer of 1 to 7.)

In a nitrogen atmosphere, a compound 1 (1 g) represented by Formula (A) and t-butanol (10 mL) were placed in a 100 mL eggplant-shaped flask and stirred until uniform to obtain a mixture. Subsequently, ethylene glycol (0.8 mL) and potassium tert-butoxide (0.2 g) were added to the mixture described above, and the mixture was stirred for 9 hours while being heated to 70° C. and cooled to 25° C.

Thereafter, the reaction product described above was washed with water by adding a fluorine-based solvent (trade name: ASAHIKLIN (registered trademark) AK-225, manufactured by Asahi Glass Co., Ltd.) to the eggplant-shaped flask described above, recovery, dehydration and filtration were carried out in the same manner as compound 1 represented by Formula (A), and the residue was separated by column chromatography.

A colorless and transparent liquid compound 2 (0.7 g) represented by Formula (B) was obtained by the above steps. The compound is a mixture of compounds where $n^1=1$ to 7.

$^1$H-NMR and $^{19}$F-NMR measurement of the obtained compound 2 was performed, and the structure was identified based on the following results.

$^1$H-NMR (acetone-$D_6$): δ [ppm]=3.30 to 4.10 (11H), 4.12 (2H)

$^{19}$F-NMR (acetone-$D_6$): δ [ppm]=−130.00 to −129.00 (12F), −127.48 (2F), −124.33 (2F), −86.42 (4F), −84.00 to −83.00 (24F)

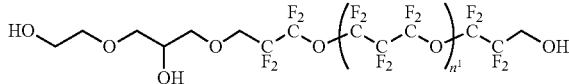

(B)

(In Formula (B), $n^1$ represents an integer of 1 to 7.)

Example 2

A colorless transparent liquid compound 3 (0.7 g) represented by Formula (C) was obtained in the same manner as compound 2 represented by Formula (B) in Example 1 except that a fluoropolyether represented by $HOCH_2CF_2CF_2O(CF_2CF_2CF_2O)_n{}^1CF_2CF_2CH_2OH$ (mixture where $m^1=1$ to 11, number-average molecular weight 1,800, molecular weight distribution: 1.2) was used instead of the fluoropolyether represented by $HOCH_2CF_2CF_2O$ $(CF_2CF_2CF_2O)_n{}^1CF_2CF_2CH_2OH$ (mixture where $n^1=1$ to 7, number-average molecular weight 1,280, molecular weight distribution 1.2). The compound is a mixture of compounds where $m^3=1$ to 11.

$^1$H-NMR and $^{19}$F-NMR measurements of the obtained compound 3 were performed and the structure was identified based on the following results.

$^1$H-NMR (acetone-$D_6$): δ [ppm]=1.79 (21-), 3.30 to 4.10. (11H), 4.12 (2H)

$^{19}$F-NMR (acetone-$D_6$): δ [ppm]=−130.00 to −129.00 (18F), −127.48 (2F), −124.33 (2F), −86.42 (4F), −84.00 to −83.00 (36F)

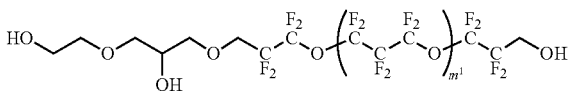

(C)

(In Formula (C), $m^1$ represents an integer of 1 to 11.)

Example 3

A colorless and transparent liquid compound 4 (0.7 g) represented by Formula (D) was obtained in the same manner as compound 2 represented by Formula (B) in Example 1 except that 1,3-propylene glycol was used instead of ethylene glycol. The compound is a mixture of compounds where $n^1=1$ to 7.

$^1$H-NMR and $^{19}$F-NMR measurements of the obtained compound 4 were performed and the structure was identified based on the following results.

$^1$H-NMR (acetone-$D_6$): δ [ppm]=1.79 (2H), 3.30 to 4.10. (11H), 4.12 (2H)

$^{19}$F-NMR (acetone-$D_6$): δ [ppm]=−130.00 to −129.00 (12F), −127.48 (2F), −124.33 (2F), −86.42 (4F), −84.00 to −83.00 (24F)

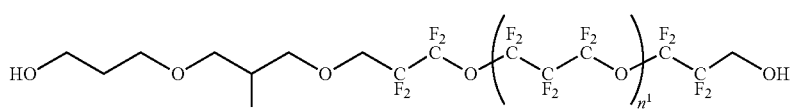

(D)

(In Formula (D), $n^1$ represents an integer of 1 to 7.)

Example 4

A colorless and transparent liquid compound 5 (0.7 g) represented by Formula (E) was obtained in the same manner as compound 2 represented by Formula (B) in Example 1 except that 1,4-butylene glycol was used instead of ethylene glycol. The compound is a mixture of compounds where $n^1=1$ to 7.

$^1$H-NMR and $^{19}$F-NMR measurements of the obtained compound 5 were performed and the structure was identified based on the following results.

$^1$H-NMR (acetone-$D_6$): δ [ppm]=1.61 (2H), 1.71 (2H), 3.30 to 4.10. (11H), 4.12 (2H)

$^{19}$F-NMR (acetone-$D_6$): δ [ppm]=−130.00 to −129.00 (12F), −127.48 (2F), −124.33 (2F), −86.42 (4F), −84.00 to −83.00 (24F)

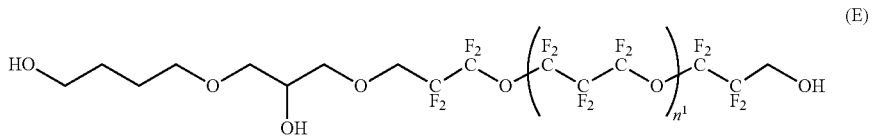

(E)

(In Formula (E), $n^1$ represents an integer of 1 to 7.)

Example 5

A colorless and transparent liquid compound 6 (6.0 g) represented by Formula (F) was obtained in the same manner as compound 1 represented by Formula (A) in Example 1 except that the amount of epibromohydrin added dropwise was changed to 6.2 g.

$^1$H-NMR and $^{19}$F-NMR measurements of the obtained compound 6 were performed and the structure was identified based on the following results.

$^1$H-NMR (acetone-D$_6$): δ [ppm]=2.60 (2H), 2.77 (2H), 3.12 (2H), 3.57 (2H), 3.98 (2H), 4.12 (4H)

$^{19}$F-NMR (acetone-D$_6$): δ [ppm]=−130.00 to −129.00 (12F), −124.33 (4F), −86.42 (4F), −84.00 to −83.00 (24F)

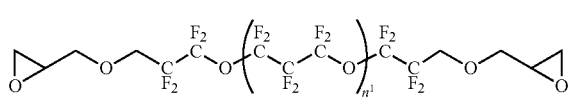

(F)

(In Formula (F), n represents an integer of 1 to 7.)

In a nitrogen atmosphere, compound 6 (1 g) represented by Formula (F) and t-butanol (10 mL) were placed in a 300 mL eggplant-shaped flask and stirred until uniform to obtain a mixture. Next, ethylene glycol (1.1 mL) and potassium tert-butoxide (0.2 g) were added to the mixture described above, and the mixture was stirred for 9 hours while being heated to 70° C., and cooled to 25° C.

Thereafter, the reaction product described above was washed with water by adding a fluorine-based solvent (trade name: ASAHIKLIN (registered trademark) AK-225, manufactured by Asahi Glass Co., Ltd.) to the eggplant-shaped flask described above, recovery, dehydration and filtration were carried out in the same manner as compound 1 represented by Formula (A), and the residue was separated by column chromatography. A colorless and transparent liquid compound 7 (0.7 g) represented by Formula (G) was obtained by the above steps. The compound is a mixture of compounds where $n^1$=1 to 7.

$^1$H-NMR and $^{19}$F-NMR measurements of the obtained compound 7 were performed and the structure was identified based on the following results.

$^1$H-NMR (acetone-D$_6$): δ [ppm]=3.30 to 4.10 (18H), 4.12 (4H)

$^{19}$F-NMR (acetone-D$_6$): δ [ppm]=−130.00 to −129.00 (12F), −124.33 (4F). −86.42 (4F), −84.00 to −83.00 (24F)

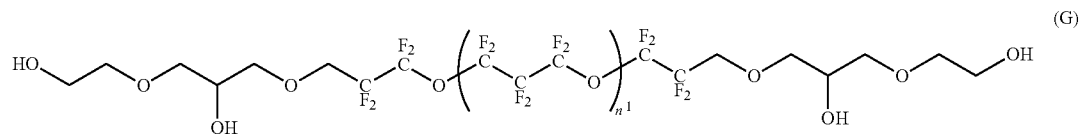

(G)

(In Formula (G), $n^1$ represents an integer of 1 to 7.)

Example 6

A colorless and transparent liquid compound 8 (0.7 g) represented by Formula (H) was obtained in the same manner as compound 7 represented by Formula (G) in Example 5 except that a fluoropolyether represented by HOCH$_2$CF$_2$CF$_2$O(CF$_2$CF$_2$CF$_2$O)$_m{}^1$CF$_2$CF$_2$CH$_2$OH (a mixture where $m^1$=1 to 11, number-average molecular weight 1,800, and molecular weight distribution: 1.2) was used instead of the fluoropolyether represented by HOCH$_2$CF$_2$CF$_2$O(CF$_2$CF$_2$CF$_2$O)$_m{}^1$CF$_2$CF$_2$CH$_2$OH (mixture of $n^1$=1 to 7, number-average molecular weight 1,280, and molecular weight distribution 1.2). The compound is a mixture of compounds where $m^1$=1 to 11.

$^1$H-NMR and $^{19}$F-NMR measurements of the obtained compound 8 were performed and the structure was identified based on the following results.

$^1$H-NMR (acetone-D$_6$): δ [ppm]=3.30 to 4.10 (18H), 4.12 (4H)

$^{19}$F-NMR (acetone-D$_6$): δ [ppm]=−130.00 to −129.00 (18F), −124.33 (4F), −86.42 (4F), −84.00 to −83.00 (36F)

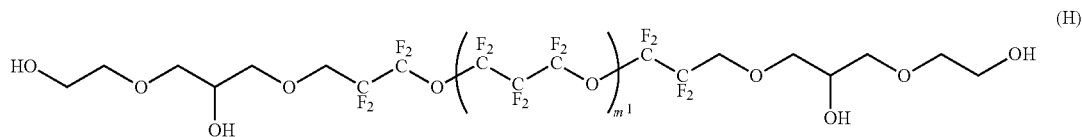

(H)

(In Formula (H), $m^1$ represents an integer of 1 to 11.)

Example 7

A colorless and transparent liquid compound 9 (0.7 g) represented by Formula (1) was obtained in the same manner as compound 7 represented by Formula (G) in Example 5 except that 1,3-propylene glycol was used instead of ethylene glycol. The compound is a mixture of compounds where $n^1$=1 to 7.

$^1$H-NMR and $^{19}$F-NMR measurements of the obtained compound 9 were performed and the structure was identified based on the following results.

$^1$H-NMR (acetone-$D_6$): δ [ppm]=1.79 (4H), 3.30 to 4.10. (18H), 4.12 (4H)

$^{19}$F-NMR (acetone-$D_6$): δ [ppm]=−130.00 to −129.00 (12F), −124.33 (4F), −86.42 (4F), −84.00 to −83.00 (24F)

manner as in compound 1 represented by Formula (A) except that a fluoropolyether represented by $HOCH_2CF_2CF_2CF_2O(CF_2CF_2CF_2O)_n{}^1CF_2CF_2CH_2OH$ in Example 1 was replaced with a fluoropolyether represented by $HOCH_2CF_2O(CF_2CF_2O)_m{}^1CF_2CH_2OH$ (a mixture where $m^1$=1 to 11, number-average molecular weight 1,330, and molecular weight distribution 1.1).

$^1$H-NMR and $^{19}$F-NMR measurements of the obtained compound 11 were performed and the structure was identified based on the following results.

$^1$H-NMR (acetone-$D_6$): δ [ppm]=2.60 (1H), 2.77 (1H), 3.12 (1H), 3.57 (1H), 3.88 (1H), 3.93 (2H), 4.08 (2H)

$^{19}$F-NMR (acetone-$D_6$): δ [ppm]=−89.50 to −88.50 (40F), −81.25 (2F), −78.50 (2F)

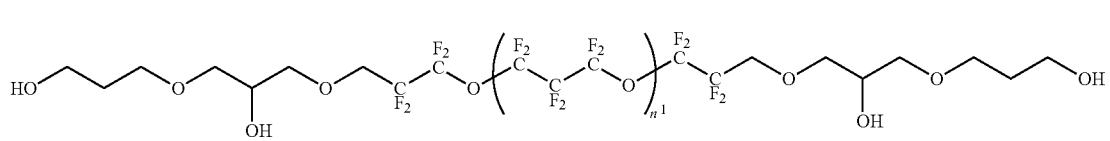

(I)

(In Formula (I), $n^1$ represents an integer of 1 to 7.)

Example 8

A colorless and transparent liquid compound 10 (0.7 g) represented by Formula (J) was obtained in the same manner as compound 7 represented by Formula (G) in Example 5 except that 1,4-butylene glycol was used instead of ethylene glycol. The compound is a mixture of compounds where $n^1$=1 to 7.

$^1$H-NMR and $^{19}$F-NMR measurements of the obtained compound 10 were performed and the structure was identified based on the following results. $^1$H-NMR (acetone-$D_6$): δ [ppm]=1.61 (4H), 1.71 (4H), 3.30 to 4.10. (18H), 4.12 (4H)

$^{19}$F-NMR (acetone-$D_6$): δ [ppm]=−130.00 to −129.00 (12F), −124.33 (4F), −86.42 (4F), −84.00 to −83.00 (24F)

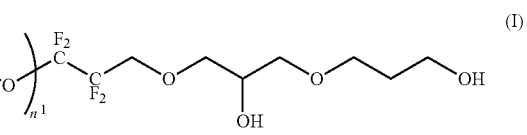

(K)

(In Formula (K), $m^1$ represents an integer of 1 to 11.)

A colorless and transparent liquid compound 12 (0.7 g) represented by Formula (L) was obtained in the same manner as compound 2 represented by Formula (B), except that compound 1 represented by Formula (A) in Example 1 was replaced with compound 11 represented by Formula (K). The compound is a mixture of compounds where $m^1$=1 to 11.

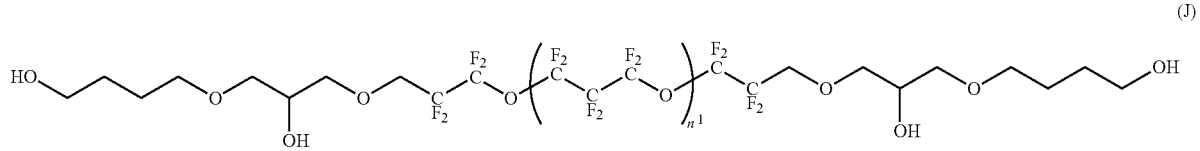

(J)

(In Formula (J), $n^1$ represents an integer of 1 to 7.)

Example 9

A colorless and transparent liquid compound 11 (5.2 g) represented by Formula (K) was obtained in the same $^1$H-NMR and $^{19}$F-NMR measurements of the obtained compound 12 were performed and the structure was identified based on the following results.

$^1$H-NMR (acetone-$D_6$): δ [ppm]=3.30 to 4.10 (11H), 4.08 (2H)

$^{19}$F-NMR (acetone-D$_6$): δ [ppm]=−89.50 to −88.50 (40F), −81.25 (2F), −78.50 (2F)

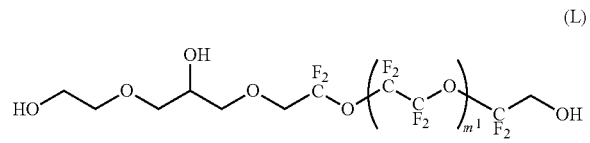

(L)

(In Formula (L), m$^1$ represents an integer of 1 to 11.)

Example 10

A colorless and transparent liquid compound 13 (0.7 g) represented by Formula (M) was obtained in the same manner as compound 3 represented by Formula (C) in Example 2 except that a fluoropolyether represented by HOCH$_2$CF$_2$O(CF$_2$CF$_2$O)$_n{}^1$CF$_2$CH$_2$OH (a mixture where l$^1$=1 to 15, number-average molecular weight 1,800, and molecular weight distribution 1.2) was used instead of the fluoropolyether represented by HOCH$_2$CF$_2$CF$_2$O(CF$_2$CF$_2$CF$_2$O)$_n{}^1$CF$_2$CF$_2$CH$_2$OH. The compound is a mixture of compounds where l$^1$=1 to 15.

$^1$H-NMR and $^{19}$F-NMR measurements of the obtained compound 13 were performed and the structure was identified based on the following results.

$^1$H-NMR (acetone-D$_6$): δ [ppm]=3.30 to 4.10 (11H), 4.08 (2H)

$^{19}$F-NMR (acetone-D$_6$): δ [ppm]=−89.50 to −88.50 (56F), −81.25 (2F), −78.50 (2F)

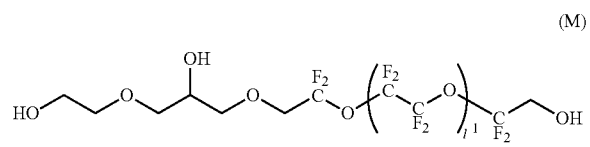

(M)

(In Formula (M), l$^1$ represents an integer of 1 to 15.)

Example 11

A colorless transparent liquid compound 14 (0.7 g) represented by Formula (N) was obtained in the same manner as compound 2 represented by Formula (B) in Example 1 except that compound 1 represented by Formula (A) in Example 1 was replaced with compound 11 represented by Formula (K) and 1,3-propylene glycol was used instead of ethylene glycol. The compound is a mixture of compounds where m$^1$=1 to 11.

$^1$H-NMR and $^{19}$F-NMR measurements of the obtained compound 14 were performed and the structure was identified based on the following results.

$^1$H-NMR (acetone-D$_6$): δ [ppm]=1.79 (2H), 3.30 to 4.10 (11H), 4.08 (2H)

$^{19}$F-NMR (acetone-D$_6$): δ [ppm]=−89.50 to −88.50 (40F), −81.25 (2F), −78.50 (2F)

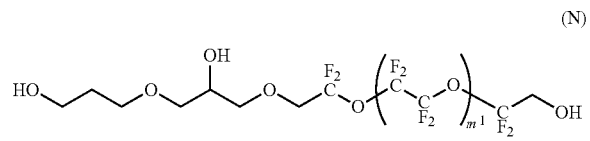

(N)

(In Formula (N), m$^1$ represents an integer of 1 to 11.)

Example 12

A colorless transparent liquid compound 15 (0.7 g) represented by Formula (0) was obtained in the same manner as compound 2 represented by Formula (B) in Example 1 except that compound 1 represented by Formula (A) in Example 1 was replaced with compound 11 represented by Formula (K) and 1,4-butylene glycol was used instead of ethylene glycol. The compound is a mixture of compounds where m$^1$=1 to 11.

$^1$H-NMR and $^{19}$F-NMR measurements of the obtained compound 15 were performed and the structure was identified based on the following results.

$^1$H-NMR (acetone-D$_6$): δ [ppm]=1.61 (2H), 1.71 (2H), 3.30 to 4.10 (11H), 4.08 (2H)

$^{19}$F-NMR (acetone-D$_6$): δ [ppm]=−89.50 to −88.50 (40F), −81.25 (2F), −78.50 (2F)

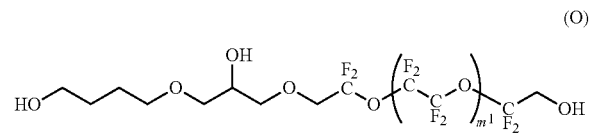

(O)

(In Formula (O), m$^1$ represents an integer of 1 to 11.)

Example 13

A colorless transparent liquid compound 16 (5.9 g) represented by Formula (P) was obtained in the same manner as compound 1 represented by Formula (A) except that the fluoropolyether represented by HOCH$_2$CF$_2$CF$_2$O(CF$_2$CF$_2$CF$_2$O)$_n{}^1$CF$_2$CF$_2$CH$_2$OH in Example 1 was replaced with fluoropolyether represented by HOCH$_2$CF$_2$O(CF$_2$CF$_2$CF$_2$O)$_m{}^1$CF$_2$CH$_2$OH (a mixture where m=1 to 11, number-average molecular weight 1,330, and molecular weight distribution 1.1) and the amount of epibromohydrin added dropwise was changed to 5.9 g.

$^1$H-NMR and $^{19}$F-NMR measurements of the obtained compound 16 were performed and the structure was identified based on the following results.

$^1$H-NMR (acetone-D$_6$): δ [ppm]=2.60 (2H), 2.77 (2H), 3.12 (2H), 3.57 (2H), 3.88 (2H), 408 (4H)

$^{19}$F-NMR (acetone-D$_6$): δ [ppm]=−89.50 to −88.50 (40F), −78.50 (4F)

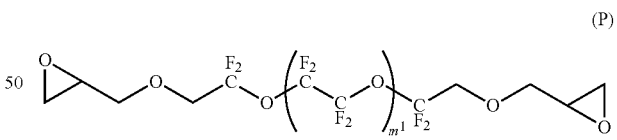

(P)

(In Formula (P), m$^1$ represents an integer of 1 to 11.)

A colorless transparent liquid compound 17 (0.7 g) represented by Formula (Q) was obtained in the same manner as compound 7 represented by Formula (G) except that compound 6 represented by Formula (F) in Example 5 was replaced with compound 16 represented by Formula (P). The compound is a mixture of compounds where m$^1$=1 to 11.

$^1$H-NMR and $^{19}$F-NMR measurements of the obtained compound 17 were performed and the structure was identified based on the following results.

$^1$H-NMR (acetone-D$_6$): δ [ppm]=3.30 to 4.10 (18H), 4.08 (4H)

$^{19}$F-NMR (acetone-D$_6$): δ [ppm]=−89.50 to −88.50 (40F), −78.50 (4F)

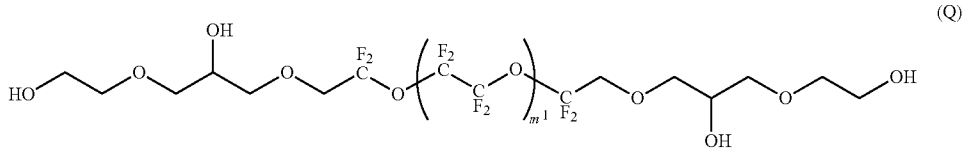

(In Formula (Q), $m^1$ represents an integer of 1 to 11.)

Example 14

A colorless and transparent liquid compound 18 (0.7 g) represented by Formula (R) was obtained in the same manner as compound 7 represented by Formula (G) in Example 5 except that a fluoropolyether represented by $HOCH_2CF_2O(CF_2CF_2O)_{l^1}CF_2CH_2OH$ (a mixture where $l^1=1$ to 15, number-average molecular weight 1,800, and molecular weight distribution 1.2) was used instead of the fluoropolyether represented by $HOCH_2CF_2CF_2O(CF_2CF_2CF_2O)_n{}^1CF_2CF_2CH_2OH$. The compound is a mixture of compounds where $l^1=1$ to 15.

$^1$H-NMR and $^{19}$F-NMR measurements of the obtained compound 18 were performed and the structure was identified based on the following results.

$^1$H-NMR (acetone-$D_6$): δ [ppm]=3.30 to 4.10 (11H), 4.08 (2H)

$^{19}$F-NMR (acetone-$D_6$): δ [ppm]=−89.50 to −88.50 (56F), −81.25 (2F), −78.50 (2F)

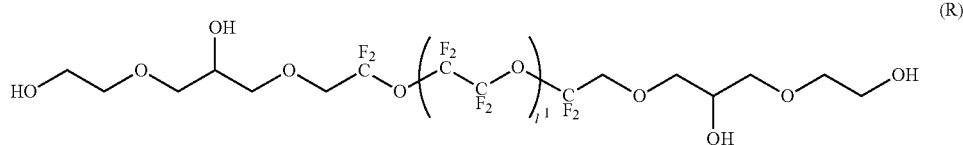

(In Formula (R), $l^1$ represents an integer of 1 to 15.)

Example 15

A colorless transparent liquid compound 19 (0.7 g) represented by Formula (S) was obtained in the same manner as compound 7 represented by Formula (G) in Example 5 except that compound 6 represented by Formula (F) in Example 5 was replaced with compound 16 represented by Formula (P) and 1,3-propylene glycol was used instead of ethylene glycol. The compound is a mixture of compounds where $m^1=1$ to 11.

$^1$H-NMR and $^{19}$F-NMR measurements of the obtained compound 19 were performed and the structure was identified based on the following results.

$^1$H-NMR (acetone-$D_6$): δ [ppm]=1.79 (4H), 3.30 to 4.10 (18H), 4.08 (4H)

$^{19}$F-NMR (acetone-$D_6$): δ [ppm]=−89.50 to −88.50 (40F), −78.50 (4F)

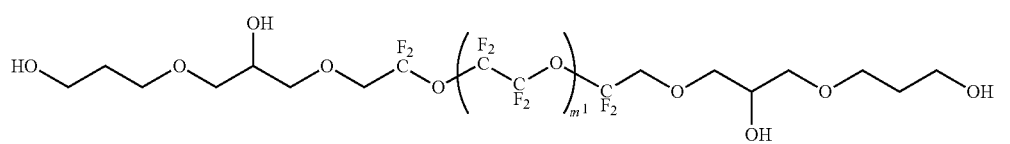

(In Formula (S), $m^1$ represents an integer of 1 to 11.)

Example 16

A colorless transparent liquid compound 20 (0.7 g) represented by Formula (T) was obtained in the same manner as compound 7 represented by Formula (G) in Example 5 except that compound 6 represented by Formula (F) in Example 5 was replaced with compound 16 represented by Formula (P) and 1,4-butylene glycol was used instead of ethylene glycol. The compound is a mixture of compounds where $m^1$=1 to 11.

$^1$H-NMR and $^{19}$F-NMR measurements of the obtained compound 20 were performed and the structure was identified based on the following results.

$^1$H-NMR (acetone-D$_6$): δ [ppm]=1.61 (4H), 1.71 (4H), 3.30 to 4.10 (18H), 4.08 (4H)

$^{19}$F-NMR (acetone-D$_6$): δ [ppm]=−89.50 to −88.50 (40F), −78.50 (4F)

distribution 1.1) was used instead of a fluoropolyether represented by HOCH$_2$CF$_2$CF$_2$O(CF$_2$CF$_2$CF$_2$O)$_n$CF$_2$CF$_2$CH$_2$OH.

$^1$H-NMR and $^{19}$F-NMR measurements of the obtained compound 21 were performed and the structure was identified based on the following results.

$^1$H-NMR (acetone-D$_6$): δ [ppm]=3.30 to 4.50 (13H)

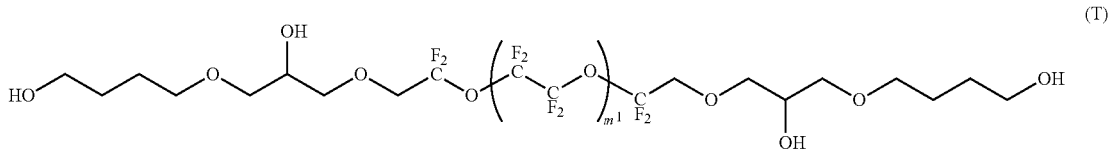

(T)

(In Formula (T), $m^1$ represents an integer of 1 to 11.)

Table 1 shows the structure obtained when applying the thus obtained compounds of Examples 1 to 16 to Formula (1) or Formula (2), the value of y in Formula (3) included in $R^2$, and the value of x when $R^1$ is Formula (4).

$^{19}$F-NMR (acetone-D$_6$): δ [ppm]=−91.15 to −88.51 (24F), −83.21 (1F), −81.22 (1F), −80.61 (1F), −78.75 (1F), −55.65 to −51.59 (12F)

TABLE 1

| Compound | | R$^1$ x[Formula (4)] | R$^2$ y[Formula (3)] |
|---|---|---|---|
| Example 1 | B | Formula (1) | 1 | 3 |
| Example 2 | C | Formula (1) | 1 | 3 |
| Example 3 | D | Formula (1) | 2 | 3 |
| Example 4 | E | Formula (1) | 3 | 3 |
| Example 5 | G | Formula (2) | 1 | 3 |
| Example 6 | H | Formula (2) | 1 | 3 |
| Example 7 | I | Formula (2) | 2 | 3 |
| Example 8 | J | Formula (2) | 3 | 3 |
| Example 9 | L | Formula (1) | 1 | 2 |
| Example 10 | M | Formula (1) | 1 | 2 |
| Example 11 | N | Formula (1) | 2 | 2 |
| Example 12 | O | Formula (1) | 3 | 2 |
| Example 13 | Q | Formula (2) | 1 | 2 |
| Example 14 | R | Formula (2) | 1 | 2 |
| Example 15 | S | Formula (2) | 2 | 2 |
| Example 16 | T | Formula (2) | 3 | 2 |

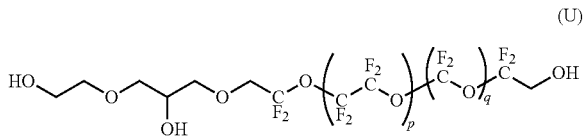

(U)

(In Formula (U), p represents an integer of 1 to 7, and q represents an integer of 1 to 7.)

Comparative Example 2

Compound 22 represented by Formula (V) was synthesized by the method described in Japanese Patent No. 4632144.

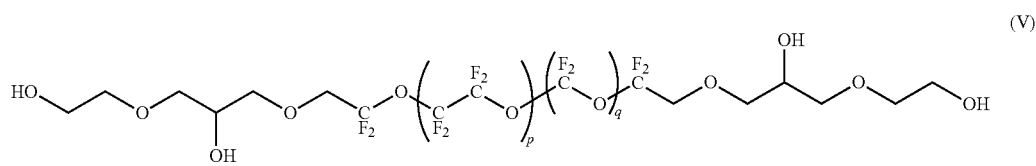

(V)

Comparative Example 1

A colorless transparent liquid compound 21 (0.7 g) represented by Formula (U) was obtained in the same manner as compound 3 represented by Formula (C) in Example 2 except that a fluoropolyether represented by HOCH$_2$CF$_2$(CF$_2$CF$_2$O)$_p$(CF$_2$O)$_q$CF$_2$CH$_2$OH (p=1 to 7, q=1 to 7, number-average molecular weight 1,300, and molecular weight (In Formula (V), p represents an integer of 1 to 7, and q represents an integer of 1 to 7.)

Comparative Example 3

Compound 23 represented by Formula (W) was synthesized by the method described in Japanese Patent No. 4632144.

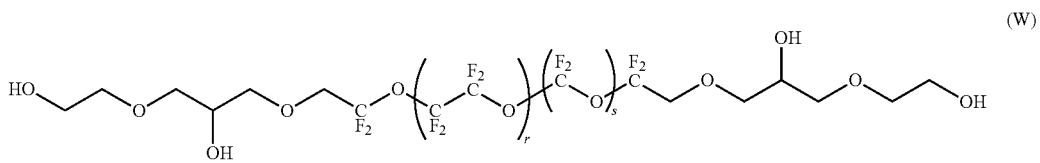

(W)

(In Formula (W), r represents an integer of 1 to 11, and s represents an integer of 1 to 1.)

The number-average molecular weights of the compounds of Examples 1 to 16 and Comparative Examples 1 to 3 thus obtained were determined by the $^1$H-NMR and $^{19}$F-NMR measurement described above. The results are shown in Table 2.

Next, a lubricating layer-forming solution was prepared using the compounds obtained in Examples 1 to 16 and Comparative Examples 1 to 3 by the following method. Using the obtained lubricating layer forming-solution, a lubricating layer of a magnetic recording medium was formed by the following method to obtain the magnetic recording media of Examples 1 to 16 and Comparative Examples 1 to 3.

[Lubricating Layer-Forming Solution]

The compounds obtained in Examples 1 to 16 and Comparative Examples 1 to 3 were each dissolved in Vertrel (registered trademark) XF (trade name, manufactured by Du Pont Mitsui Fluorochemicals Co., Ltd.) which is a fluorine-based solvent and diluted with Vertrel, such that the film thickness when coated on the protective layer was 9 Å to 11 Å, to form a lubricating layer-forming solution.

[Magnetic Recording Medium]

A magnetic recording medium was prepared in which an adhesive layer, a soft magnetic layer, a first underlayer, a second underlayer, a magnetic layer, and a protective layer were provided in order on a substrate having a diameter of 65 mm. The protective layer was formed of carbon.

The lubricating layer-forming solutions of Examples 1 to 16 and Comparative Examples 1 to 3 were coated by a dipping method onto the protective layer of the magnetic recording medium on which the respective layers up to the protective layer were formed. The dipping method was carried out under conditions of an immersion speed of 10 mm/sec, a dipping time of 30 sec, and a pulling rate of 1.2 min/sec.

Thereafter, the magnetic recording medium coated with the lubricating layer-forming solution was placed in a thermostat at 120° C. and heated for 10 minutes to remove the solvent in the lubricating layer-forming solution. By the above, a lubricating layer was formed on the protective layer to obtain a magnetic recording medium.

The film thicknesses of the lubricating layers of the magnetic recording media of Examples 1 to 16 and Comparative Examples 1 to 3 thus obtained were measured using FT-IR (trade name: Nicolet iS 50, manufactured by Thermo Fisher Scientific). The results are shown in Table 2.

In addition, the magnetic recording media of Examples 1 to 16 and Comparative Examples 1 to 3 were subjected to bond ratio measurement and a pick-up suppression test and evaluated by the following methods. The results are shown in Table 2.

(Measurement of Adhesion (Bond Ratio) Between Lubricating Layer and Protective Layer)

The magnetic recording medium having the lubricating layer formed thereon was immersed in Vertrel as a solvent for 10 minutes and was washed by a pulling up method. The speed of immersing the magnetic recording medium in the solvent was 10 mm/sec, and the pulling up rate was 1.2 mm/sec.

Thereafter, the film thickness of the lubricating layer was measured by the same method as the measurement of the film thickness of the lubricating layer which was performed before cleaning.

Then, the bonding ratio (bond ratio) of the lubricant was calculated from the ratio ((B/A)×100(%)) of A to B, in which the film thickness of the lubricating layer before cleaning is A, and the film thickness of the lubricating layer after washing (after solvent immersion) is B. Using the calculated bond ratio, the adhesion between the lubricating layer and the protective layer was evaluated according to the following criteria.

[Adhesion (Bond Ratio) Evaluation]

C: Bond ratio is 50% or more

D: Bond ratio is less than 50%

(Pick-up Suppression Test)

A magnetic recording medium and a magnetic head were mounted on a spinstand, and the magnetic head was floated at a fixed point for 10 minutes under reduced pressure (approximately 250 torr) at room temperature. Thereafter, the surface of the magnetic head facing the magnetic recording medium (the surface of the lubricating layer) was analyzed using an Electron Spectroscopy for Chemical Analysis (ESCA) analyzer. The adhesion amount of the lubricant to the magnetic head was evaluated according to the criteria shown in Table 3 from the intensity of the fluorine-derived peak (signal intensity (a.u.)) measured by ESCA. The results are shown in Table 2.

TABLE 2

|  | Compound | Number-average Molecular Weight | Film Thickness (Å) | Bonding Ratio | Pick-up Suppression Test | Overall Evaluation |
| --- | --- | --- | --- | --- | --- | --- |
| Example 1 | B | 1410 | 9.7 | 66 C | A | A |
| Example 2 | C | 1932 | 10.5 | 69 C | A | A |
| Example 3 | D | 1423 | 10 | 63 C | A | A |
| Example 4 | E | 1430 | 10 | 65 C | A | A |
| Example 5 | G | 1520 | 10 | 75 C | A | A |
| Example 6 | H | 2030 | 10.5 | 77 C | A | A |
| Example 7 | I | 1552 | 10 | 73 C | A | A |

TABLE 2-continued

|  | Compound | Number-average Molecular Weight | Film Thickness (Å) | Bonding Ratio | Pick-up Suppression Test | Overall Evaluation |
|---|---|---|---|---|---|---|
| Example 8 | J | 1582 | 10 | 75 | C | A | A |
| Example 9 | L | 1453 | 10 | 65 | C | A | A |
| Example 10 | M | 1930 | 10.5 | 68 | C | A | A |
| Example 11 | N | 1483 | 10 | 65 | C | A | A |
| Example 12 | O | 1488 | 10 | 66 | C | A | A |
| Example 13 | Q | 1572 | 10 | 77 | C | A | A |
| Example 14 | R | 2021 | 10.5 | 79 | C | A | A |
| Example 15 | S | 1601 | 10 | 74 | C | A | A |
| Example 16 | T | 1634 | 10 | 75 | C | A | A |
| Comparative Example 1 | U | 1458 | 10 | 40 | D | C | C |
| Comparative Example 2 | V | 1612 | 10 | 50 | C | C | C |
| Comparative Example 3 | W | 2180 | 10.5 | 53 | C | C | C |

TABLE 3

| Evaluation | ESCA Signal Strength (a.u.) | Evaluation Criteria |
|---|---|---|
| A | 500 or less | There was no lubricant adhered to the head and there was no change in the signal strength. |
| B | Over 500 to 1,000 | There was a small amount of lubricant adhered to the head, and the signal strength was low. |
| C | Over 1,000 | There was a large amount of lubricant adhered to the head, and the signal strength was high. |

As shown in Table 2, in Examples 1 to 16, the evaluation results of the adhesion (bond ratio) between the lubricating layer and the protective layer and the evaluation results of the pick-up suppression test were all good. Accordingly, it was found that forming the lubricating layer using the lubricant for the magnetic recording medium including the compounds of Examples 1 to 16 on the protective layer of the magnetic recording medium obtained a lubricating layer which was excellent in adhesion with the protective layer and which did not easily cause pick-up even when the thickness was as thin as 9 Å to 11 Å.

On the other hand, as shown in Table 2, in Comparative Examples 1 to 3, the bond ratios were smaller than those of Examples 1 to 16. In addition, in Comparative Examples 1 to 3, the evaluation result of the pick-up suppression test was C.

It is presumed that these results indicate that since the fluorine-containing ether compound used in Examples 1 to 16 includes a PFPE chain represented by Formula (3) having a repeating unit formed of a linear fluorinated alkyl ether group, the PFPE chain has rigidity compared to the fluorine-containing ether compound used in Comparative Examples 1 to 3, and the adhesion to the protective layer becomes stronger.

In addition, as shown in Table 2, in Examples 5 to 8 in which $R^3$ is $R^1$ (Formula (2)), the bonding rate was higher in comparison with Examples 1 to 4 in which $R^3$ is a hydroxyl group. In addition, in Examples 13 to 16 in which $R^3$ is $R^1$ (Formula (2)), the bond ratio was higher than in Examples 9 to 12 in which $R^3$ is a hydroxyl group. From these results, it was found that arranging $R^1$ at both ends of $R^2$ further improves the adhesion.

INDUSTRIAL APPLICABILITY

Using the lubricant for a magnetic recording medium including the fluorine-containing ether compound of the present invention makes it possible to obtain a lubricating layer which is excellent in adhesion to the protective layer and does not easily cause pick-up even when the thickness is reduced.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

EXPLANATION OF REFERENCES

10 MAGNETIC RECORDING MEDIUM
11 SUBSTRATE
12 ADHESIVE LAYER
13 SOFT MAGNETIC LAYER
14 FIRST UNDERLAYER
15 SECOND UNDERLAYER
16 MAGNETIC LAYER
17 PROTECTIVE LAYER
18 LUBRICATING LAYER

What is claimed is:

1. A fluorine-containing ether compound represented by Formula (1), $$R^1-CH_2-R^2-CH_2-R^3 \quad (1)$$

(In Formula (1), $R^1$ is an organic end group having 3 or more carbon atoms which includes two or more polar groups with each polar group being bonded to different carbon atoms and the carbon atoms to which the polar groups are bonded being bonded to each other via a linking group including the carbon atoms which are not bonded to the polar groups, $R^2$ includes a perfluoropolyether chain represented by Formula (3), and $R^3$ is a hydroxyl group or $R^1$)

$$-(CF_2)_{y-1}-O-((CF_2)_yO)_z-(CF_2)_{y-1}- \quad (3)$$

(In Formula (3), y represents an integer of 3 to 4, and z represents an integer of 1 to 30).

2. A fluorine-containing ether compound represented by Formula (2), $$R^1-CH_2-R^2-CH_2-R^1 \quad (2)$$

(In Formula (2), $R^1$ is an organic end group having 3 or more carbon atoms which includes two or more polar groups with each polar group being bonded to different carbon atoms and the carbon atoms to which the polar groups are bonded being bonded to each other via a linking group including the carbon atoms which are not bonded to the polar groups, and $R^2$ includes a perfluoropolyether chain represented by Formula (3),)

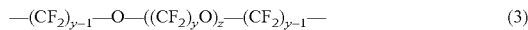   (3)

(In Formula (3), y represents an integer of 3 to 4, and z represents an integer of 1 to 30).

3. The fluorine-containing ether compound according to claim 1,
wherein each of the two or more polar groups included in $R^1$ is a hydroxyl group.

4. The fluorine-containing ether compound according to claim 1,
wherein $R^1$ has an ether bond (—O—).

5. The fluorine-containing ether compound according to claim 1,
wherein $R^1$ is an end group of Formula (4),

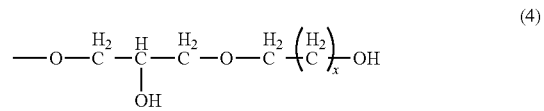

(In Formula (4), x represents an integer of 1 to 3).

6. The fluorine-containing ether compound according to claim 1,
wherein the compound in Formula (1) is represented by Formula (5),

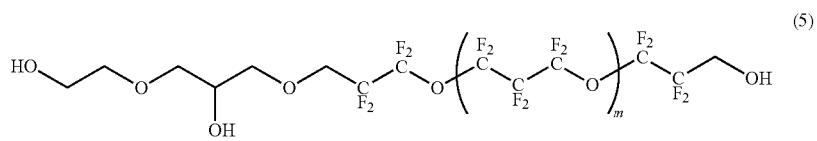

(In Formula (5), m represents an integer of 1 to 11).

7. The fluorine-containing ether compound according to claim 1,
wherein the compound in Formula (1) is represented by Formula (6),

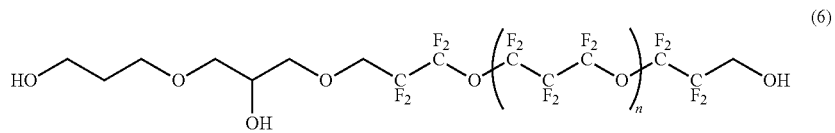

(In Formula (6), n represents an integer of 1 to 7).

8. The fluorine-containing ether compound according to claim 1,
wherein the compound in Formula (1) is represented by Formula (7),

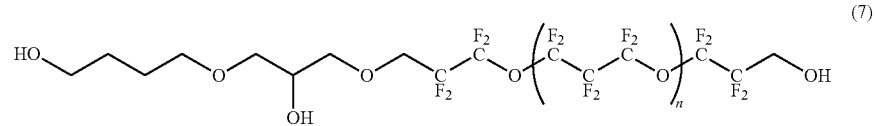

(In Formula (7), n represents an integer of 1 to 7).

9. The fluorine-containing ether compound according to claim 2,
wherein the compound in Formula (2) is represented by Formula (8),

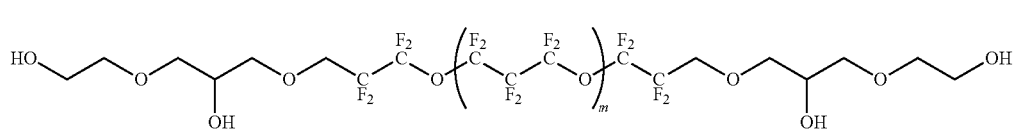

(In Formula (8), m represents an integer of 1 to 11).

10. The fluorine-containing ether compound according to claim 2,
wherein the compound in Formula (2) is represented by Formula (9),

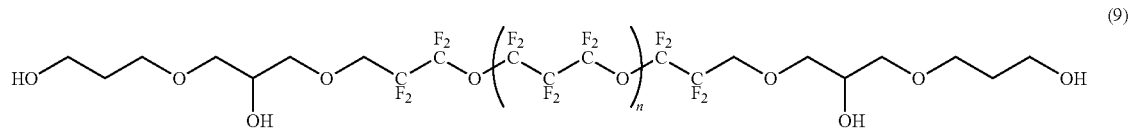

(9)

(In Formula (9), n represents an integer of 1 to 7).

11. The fluorine-containing ether compound according to claim 2,
wherein the compound in Formula (2) is represented by Formula (10),

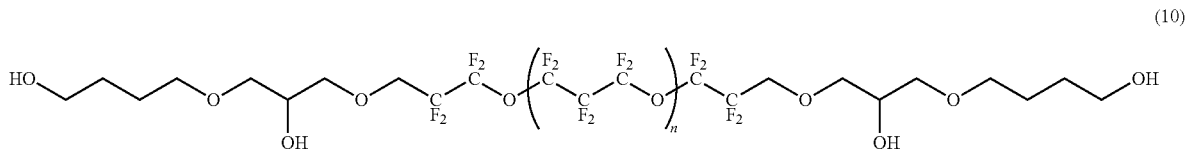

(10)

(In Formula (10), n represents an integer of 1 to 7).

12. The fluorine-containing ether compound according to claim 1,
wherein a number-average molecular weight is in a range of 800 to 10,000.

13. A lubricant for a magnetic recording medium, comprising:
the fluorine-containing ether compound according to claim 1.

14. A magnetic recording medium, comprising:
at least a magnetic layer;
a protective layer; and
a lubricating layer, which are sequentially provided on a substrate,
wherein the lubricating layer includes the fluorine-containing ether compound according to claim 1.

15. A fluorine-containing ether compound represented by Formula (1), $$R^1-CH_2-R^2-CH_2-R^3 \quad (1)$$

(In Formula (1), $R^1$ is an end group of Formula (4), $R^2$ includes a perfluoropolyether chain represented by Formula (3), and $R^3$ is a hydroxyl group or $R^1$)

(3);

(In Formula (3), y represents an integer of 2 to 4, and z represents an integer of 1 to 30),

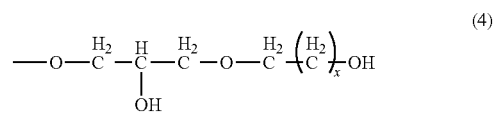

(4)

(In Formula (4), x represents an integer of 2 to 3).

16. A lubricant for a magnetic recording medium, comprising:
the fluorine-containing ether compound according to claim 15.

17. A magnetic recording medium, comprising:
at least a magnetic layer;
a protective layer; and
a lubricating layer, which are sequentially provided on a substrate,
wherein the lubricating layer includes the fluorine-containing ether compound according to claim 15.

* * * * *